(12) United States Patent
Liu et al.

(10) Patent No.: US 12,357,257 B2
(45) Date of Patent: Jul. 15, 2025

(54) CONE BEAM BREAST COMPUTED TOMOGRAPHY WITH PATIENT SUPPORT SUBSYSTEM

(71) Applicant: Koning Corporation, Norcross, GA (US)

(72) Inventors: Shaohua Liu, Atlanta, GA (US); Ruola Ning, Atlanta, GA (US)

(*) Notice: Subject to any disclaimer, the term of this patent is extended or adjusted under 35 U.S.C. 154(b) by 0 days.

(21) Appl. No.: 18/914,215

(22) Filed: Oct. 13, 2024

(65) Prior Publication Data

US 2025/0032068 A1 Jan. 30, 2025

Related U.S. Application Data

(63) Continuation of application No. PCT/US2023/018378, filed on Apr. 12, 2023.

(60) Provisional application No. 63/331,153, filed on Apr. 14, 2022, provisional application No. 63/401,475, filed on Aug. 26, 2022, provisional application No. 63/401,493, filed on Aug. 26, 2022, provisional application No. 63/401,513, filed on Aug. 26, 2022, provisional application No. 63/401,546, filed on Aug. 26, 2022, provisional application No. 63/401,548, filed on Aug. 26, 2022, provisional application No. 63/430,571, filed on Dec. 6, 2022.

(51) Int. Cl.
| | |
|---|---|
| A61B 6/04 | (2006.01) |
| A61B 6/03 | (2006.01) |
| A61B 6/40 | (2024.01) |
| A61B 6/50 | (2024.01) |
| A61B 8/08 | (2006.01) |
| G06T 7/00 | (2017.01) |

(52) U.S. Cl.
CPC .............. *A61B 6/502* (2013.01); *A61B 6/032* (2013.01); *A61B 6/035* (2013.01); *A61B 6/0435* (2013.01); *A61B 6/0478* (2013.01); *A61B 6/0487* (2020.08); *A61B 6/4085* (2013.01); *A61B 8/0825* (2013.01); *G06T 7/00* (2013.01); *G06T 2207/30068* (2013.01)

(58) Field of Classification Search
CPC ..... A61B 6/0435; A61B 6/032; A61B 6/0478; A61B 6/0487; A61B 6/4085; A61B 6/502
See application file for complete search history.

(56) References Cited

U.S. PATENT DOCUMENTS

| | | | |
|---|---|---|---|
| 6,504,892 | B1 | 1/2003 | Ning |
| 6,987,831 | B2 | 1/2006 | Ning |
| 11,191,502 | B2 | 12/2021 | Smith et al. |
| 2012/0029338 | A1 | 2/2012 | Kuo et al. |
| 2012/0069959 | A1 | 3/2012 | Hoernig |

(Continued)

OTHER PUBLICATIONS

Crotty et al., Investigating Novel Patient Bed Designs for Use in a Hybrid Dual Modality Dedicated 3D Breast Imaging System; Medical Imaging 2007: Physics of Medical Imaging, edited by Jiang Hsieh, Michael J. Flynn, Proc. Of SPIE vol. 6510, 65101H, (2007).

*Primary Examiner* — Courtney D Thomas
(74) *Attorney, Agent, or Firm* — Bergman LLC; Michael Bergman

(57) ABSTRACT

A cone beam breast computer tomographic scanning system includes a vertical plane gantry and a patient support subsystem, where the patient support subsystem has a patient support saddle for patient positioning during imaging.

20 Claims, 18 Drawing Sheets

(56) References Cited

U.S. PATENT DOCUMENTS

2014/0254750 A1\* 9/2014 Yoshimura ............ A61B 6/035
378/20
2020/0170603 A1 6/2020 Bailey et al.

\* cited by examiner

CONE BEAM BREAST COMPUTED TOMOGRAPHY WITH PATIENT SUPPORT SUBSYSTEM

CROSS-REFERENCE TO RELATED APPLICATIONS

The present application is a continuation of PCT patent application PCT/US2023/018378 filed on Apr. 12, 2023, which claims the benefit of provisional patent applications OMNIBUS DISCLOSURE, set forth in an application for Letters Patent of the United States already filed on Apr. 14, 2022 as U.S. Provisional Application No. 63/331,153, and FIXTURING AND SUPPORT FOR MEDICAL IMAGING, set forth in an application for Letters Patent of the United States already filed on Aug. 26, 2022 as U.S. Provisional Application No. 63/401,475, and ERGONOMIC IMPROVEMENTS IN CONE BEAM BREAST COMPUTED TOMOGRAPHY, set forth in an application for Letters Patent of the United States already filed on Aug. 26, 2022 as U.S. Provisional Application No. 63/401,493, and STATIONARY DETAIL IMAGING IN CONE BEAM BREAST COMPUTED TOMOGRAPHY, set forth in an application for Letters Patent of the United States already filed on Aug. 26, 2022 as U.S. Provisional Application No. 63/401,513, and CONE BEAM BREAST COMPUTED TOMOGRAPHY WITH PATIENT SUPPORT SUBSYSTEM, set forth in an application for Letters Patent of the United States already filed on Aug. 26, 2022 as U.S. Provisional Application No. 63/401,546, and, CONE BEAM BREAST COMPUTED TOMOGRAPHY WITH PIVOTAL GANTRY SUBSYSTEM, set forth in an application for Letters Patent of the United States already filed on Aug. 26, 2022 as U.S. Provisional Application No. 63/401,548, and ULTRASONIC HYBRID IMAGING IN CONE BEAM BREAST COMPUTED TOMOGRAPHY, set forth in an application for Letters Patent of the United States already filed on Dec. 6, 2022 as U.S. Provisional Application No. 63/430,571, the disclosures of all of which are herewith incorporated by reference in their entireties.

FIELD OF THE INVENTION

The present invention relates to the field of cone beam tomographic imaging, and in particular to the field of patient ergonomics in cone beam breast tomographic imaging.

SUMMARY

According to the National Cancer Institute, one out of eight women will be diagnosed with breast cancer in her lifetime. And while a reduction in mortality from breast cancer is evident in published reports, each year 40,000 women will die of the disease.

The optimal breast imaging technique detects tumor masses when they are small, preferably less than 10 mm in diameter. It is reported that 93% of women with mammographically detected invasive breast carcinoma 1-10 mm have a 16-year survival rate. In addition, as the diameter of the tumor at detection decreases, the probability of metastasis declines sharply. If a breast tumor is detected when it is 10 mm or less, the probability of metastasis will be equal to 7.31%. If a 4 mm carcinoma is detected, the metastatic probability will be decreased by more than a factor of 10, to 0.617%.

Although mammography, which on average can detect cancers about 12 mm in size, is the most effective tool for the early detection of breast cancer currently available, mammography has relatively low sensitivity to small breast cancers (under several millimeters). Specificity and the positive predictive value of mammography remain limited owing to structure and tissue overlap. The limited sensitivity and specificity in breast cancer detection of mammography are due to its poor contrast detectability, which is common for all types of projection imaging techniques (projection imaging can only have up to 10% contrast detectability), and mammography initially detects only 65-70% of breast cancers. The sensitivity of mammography is further reduced to as low as 30% in the dense breast. Digital mammography (DM) was developed to try to overcome the limitations inherent in screen-film mammography (SFM) by providing improved contrast resolution and digital image processing; however, a large-scale clinical trial, the Digital Mammographic Imaging Screening Trial (DMIST), showed that the rates of false positives for DM and SFM were the same.

The relatively low specificity of mammography leads to biopsy for indeterminate cases, despite the disadvantages of added cost and the stress it imposes on patients. Nearly 80% of the over one million breast biopsies performed annually in the U.S. to evaluate suspicious mammographic findings are benign, burdening patients with excessive anxiety and the healthcare system with tremendous cost. There is a need for more accurate characterization of breast lesions in order to reduce the biopsy rate and the false-positive rate of pre-biopsy mammograms.

The results of phantom studies indicate that Cone Beam Breast Computed Tomography (CBBCT) can achieve a spatial resolution up to about 2.8 lp/mm, allowing detection of a 2 mm carcinoma and microcalcifications about 0.2 mm in size for an average size breast (about 13 cm in diameter at the chest wall) with a total dose of about 5 mGy. This dose is less than that of a single mammography exam, assuming two views are required for each breast.

The image quality of CBBCT for visualizing breast tissues, breast tumors and calcifications is excellent, and coverage of the breast, including the chest wall region, is at least equivalent to mammography. Visualization of major blood vessels is very good without using a contrast agent. Accordingly, CBBCT offers significant improvement in detecting and biopsying suspected lesions in a patient.

While the imaging benefits of CBBCT are remarkable, in many ways, the ergonomic advantages of the technology are just as important. For example, in many CBBCT procedures, an image can be acquired without requiring the compression of the breast tissue generally associated with mammography.

It is characteristic of mammography, for example, that breast imaging is preceded by insertion of a patient's breast into a fixturing apparatus that significantly compresses breast tissue in a direction transverse to a breast longitudinal axis. Patients widely report physical and psychological discomfort related to the degree of compression required for conventional mammography, and studies have shown that this discomfort is a contributing factor to low rates of screening and diagnostic mammography among patients generally and, in particular, among some ethnic and cultural populations.

Moreover, the breast compression associated with mammography can result in a displacement of breast tissue that makes the later localization of features such as lesions and calcifications, for purposes of biopsy and lumpectomy procedures, more difficult.

Additional improvements in CBBCT imaging presented herewith offer the potential to expand on its imaging benefits and offer ergonomic improvements that are likewise highly beneficial. Among these improvements are technical improvements, and methods and apparatus that facilitate presentation of the patient to the CBBCT system. These include loading apparatus, patient seating facilities, and equipment arrangements and configurations that improve comfort and ease of presentation of the patient to the machine for both the patient, and for technical and medical personnel.

In current practice, a patient undergoing CBBCT lies prone on a table. A subject breast is disposed downward through an aperture in an upper surface of the table, depending from the chest wall into an imaging chamber disposed under the table. The position of the breast within the imaging chamber is maintained by the patient remaining stationary as they lie on the surface of the table.

An imaging apparatus is coupled to a mobile gantry which is supported on a bearing device for rotation about an axis of rotation. The axis of rotation is disposed in a generally vertical orientation and passes through the aperture of the table. Preferably, an approximate centroid of the breast to be imaged is arranged such that the axis of rotation passes through the approximate centroid.

During imaging, the mobile gantry rotates around the axis of rotation, bringing the imaging apparatus through at least a portion of a circular path. As it traverses this path, the imaging apparatus emits a series of x-ray pulses and captures corresponding image data which is processed to prepare a tomographic model of the breast.

Notwithstanding the many benefits and advantages of CBBCT, there are some patients who find it difficult or impossible to assume a prone position on a patient table. Such patients may be unable to locate themselves properly on the table, or to dispose the breast to be imaged through the aperture as necessary. Patients who are elderly, obese, pregnant, or disabled, as well as those suffering from paralysis or amputation, among other ailments, are among the many for whom the act of climbing onto a table and lying down in a specific prone position is prohibitively difficult.

The inventors of the present invention, having given long and careful consideration to the problems associated with breast imaging, with CBBCT imaging and, in particular, to questions of CBBCT ergonomics, have developed new and useful systems, apparatus and methods that represent a substantial improvement over previously known approaches. The present invention includes apparatus, and corresponding systems and methods, for the entry of the patient into the CBBCT system, and for support of the patient during the tomographic imaging process.

Accordingly, in certain embodiments of the present invention, a CBBCT system is provided that is arranged for upright patient positioning. In certain embodiments of the invention, a patient is provided with a saddle for support during scanning in an upright position. In certain embodiments of the invention, the saddle is arranged to pivot so as to facilitate patient entry. In certain embodiments of the invention, the gantry is adapted to move linearly toward a patient after positioning for scanning. In certain embodiments of the invention, the patient is moved along with the saddle towards the gantry after positioning for scanning.

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention. It will be apparent to one skilled in the art, however, that the present invention may be practiced without these specific details. In other instances, well-known structures and devices are shown in block diagram form in order to avoid unnecessarily obscuring the substance disclosed. These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art will appreciate that the figures taken together reflect various embodiments exemplifying the invention.

Correspondingly, references throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" at various places throughout the specification are not necessarily all referring to the same embodiment. Furthermore, the particular features, structures, or characteristics will be combined in any suitable manner in one or more embodiments.

DETAILED DESCRIPTION

The following description is provided to enable any person skilled in the art to make and use the disclosed inventions, and sets forth the best modes presently contemplated by the inventors of carrying out their inventions. In the following description, for purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the substance disclosed.

It should be noted that while any of the embodiments described for exemplary purposes below will identify specific elements and combinations of elements, these examples are not intended to be determinative. Rather, discrete elements will, in appropriate circumstances, be combined into integral elements and/or assemblies. Further, the present disclosure of aspects and features of particular elements described herewith as integral, should be understood to convey also the disclosure of individual elements and assemblies providing the same characteristics and/or functionality.

Figure 1:
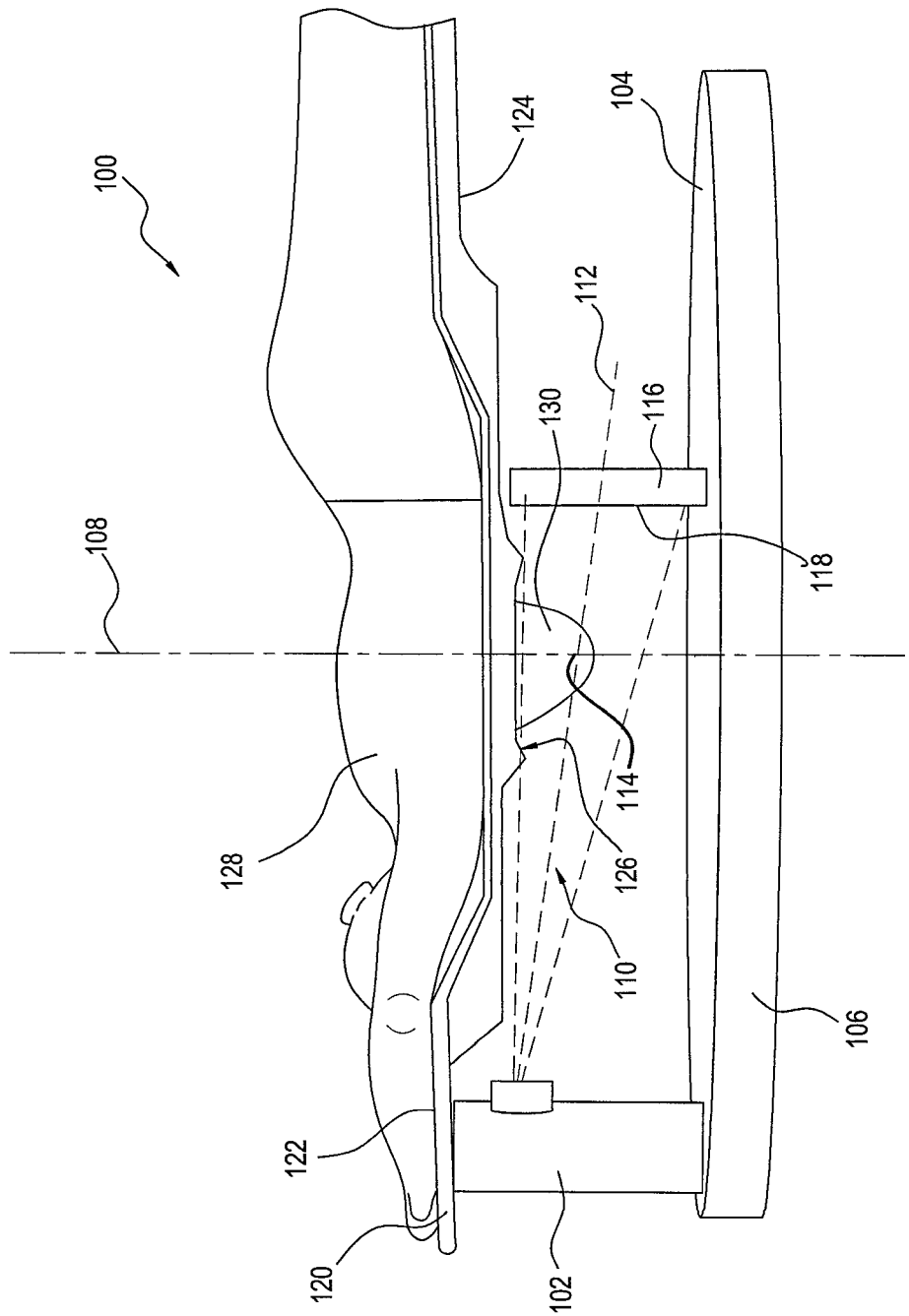
FIG. 1 shows, in cutaway perspective view, a portion of an exemplary CBBCT imaging system.

FIG. 1 shows, in cutaway perspective view, a portion of an exemplary CBBCT imaging system 100. The system 100 includes an x-ray source 102. The x-ray source 102 is mounted on an upper surface 104 of a rotating gantry 106. The rotating gantry 106 is supported by a bearing, and arranged for rotation about an axis of rotation 108.

The x-ray source 102 is configured to emit a beam of x-rays 110. The beam of x-rays 110 defines a beam longitudinal axis 112 that, in the illustrated embodiment, intersects (at 114) the axis of rotation 108.

In certain embodiments of the invention, beam 110 is configured as a cone beam. In certain configurations, a cross-section of the beam 110 taken transverse to the longitudinal axis 112 defines a disk of substantially uniform x-ray intensity with a substantially circular perimeter.

In other configurations within the scope of the invention, a cross-section of the beam 110 taken transverse to the longitudinal axis 112 defines a region of substantially uniform x-ray intensity with a substantially circular perimeter save for a portion of the disc outwardly of a chord of said circular perimeter. As will be appreciated on consideration of the further disclosure below, in certain embodiments, the chord will be disposed in generally parallel spaced relation to a lower surface of a patient table.

Accordingly, in certain configurations, a cross-section of the beam 110 taken transverse to the longitudinal axis 112 defines a truncated disk of substantially uniform x-ray intensity with a substantially truncated circular perimeter (i.e., a perimeter that is circular except for a horizontal chord of the circle at its upper periphery). This configuration optimizes imaging of the breast while minimizing irradiation of chest wall tissue above the breast. It is implemented, in certain embodiments, by the placement of an x-ray-opaque collimating plate across a portion of an otherwise circular-cross-section beam generated by the x-ray source.

In still further configurations within the scope of the invention, a cross-section of the beam 110 taken transverse to the longitudinal axis 112 defines a region of substantially uniform x-ray intensity with a polygonal perimeter, where the polygonal perimeter will, in respective embodiments and configurations, include any of a triangular perimeter, a rectangular perimeter, a pentagonal perimeter, hexagonal perimeter, a perimeter of any higher geometric shape, or a perimeter having any arbitrary curve or combination of line segments and curves according to the demands of a particular application. Moreover, it will be appreciated that any of the cross-sectional configurations described above may define a beam having a nonuniform intensity including, without limitation an intensity that falls to zero in a region, or certain regions, of the cross-section.

An x-ray detector 116 is also mounted on the upper surface 104 of the rotating gantry 106. In one exemplary embodiment, the x-ray detector 116 includes a flat panel detector having a generally planar receiving surface 118. Receiving surface 118 is disposed generally transverse to longitudinal axis 112 and on the opposite side of axis of rotation 108 from the x-ray source 102. It will be appreciated by one of skill in the art that the configuration described is merely exemplary of many possible arrangements in which the x-ray source, the x-ray detector, and any other component of the system, may be supported from above, from a side, or in any other way appropriate to achieving the desired function, and that the shape and configuration of the gantry, and of the x-ray detector, will likewise assume any appropriate form in respective embodiments of the invention.

Rotation of the gantry 106 about axis of rotation 108 during operation of the imaging system 100 will result in the receiving surface 118 following a transit path about axis of rotation 108. In a typical configuration, the transit path will include at least a portion of a circle disposed transverse to, and centered at, axis of rotation 108. It should be noted, however, that other transit paths are considered to be within the scope of the invention, and to be disclosed herewith.

In certain embodiments of the invention, one or both of the x-ray source 102 and the x-ray detector 116 are arranged so that their respective positions on the upper surface 104 of gantry 106 are adjustable. For example, the x-ray source 102 and the x-ray detector 116 may be adjustable in a radial direction (i.e., degree of freedom) with respect to axis of rotation 108, in a circumferential direction (i.e., degree of freedom) with respect to axis of rotation 108, in a direction (i.e., degree of freedom) towards or away from gantry surface 104, or in any other manner deemed beneficial by the designer or user of a particular apparatus embodying the invention.

A patient table 120 includes an upper surface 122 and a lower surface 124. An aperture 126 communicates between the upper surface 122 and lower surface 124 of the table. The upper surface 122 is arranged to support a patient 128, typically with the patient lying prone on the upper surface 122, as illustrated. In this arrangement, a breast 130 of the patient is disposed pendant from the patient's chest wall downwardly through aperture 126.

In operation, the gantry 106 rotates about axis of rotation 108, carrying x-ray source 102 and x-ray detector 116 in transit in a path around the patient's breast. During this transit, x-ray image data is captured by operation of the x-ray detector 116 in conjunction with corresponding interface electronics and computer systems. The x-ray image data corresponds to a plurality of x-ray images taken at respective angular locations about axis of rotation 108. Taken together, the x-ray image data, or a subset of the same, is processed to provide information about the internal state of the breast.

Figure 2:
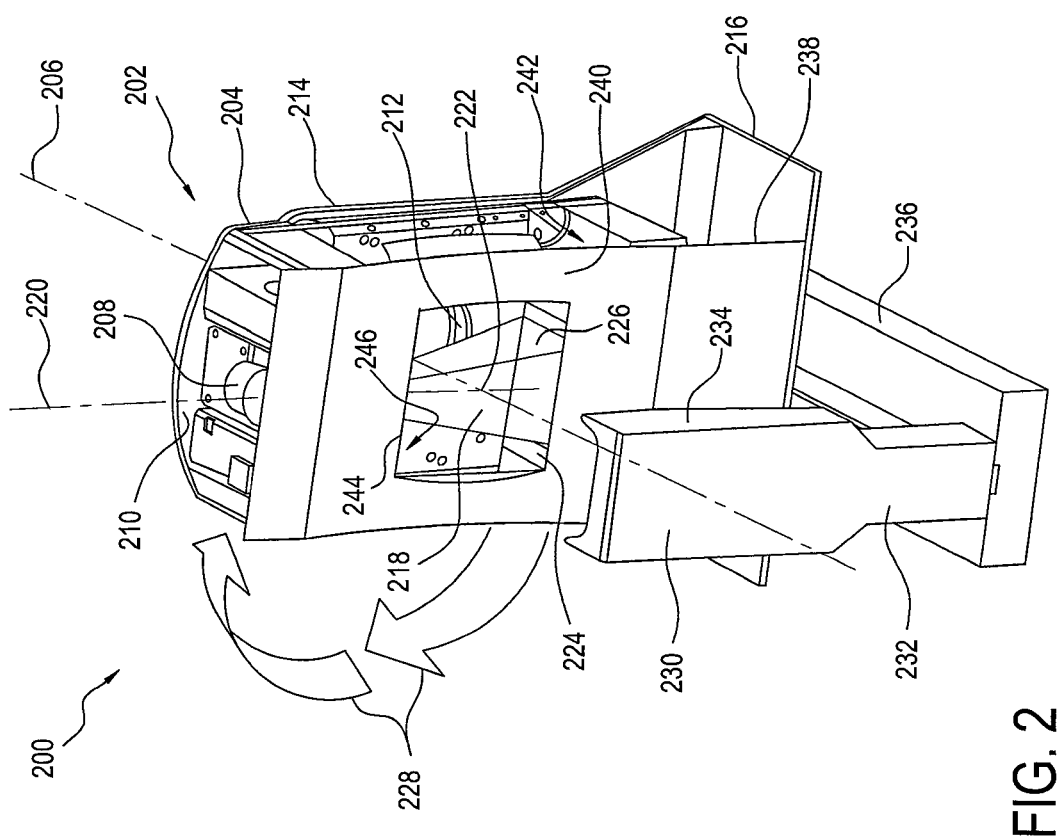
FIG. 2 shows, in elevated schematic perspective view, a portion of an exemplary CBBCT imaging system, including a vertical plane gantry subsystem prepared according to principles of the invention.

FIG. 2 shows, in elevated schematic perspective view, a portion of an exemplary CBBCT imaging system 200, including a vertical plane gantry subsystem 202. The vertical plane gantry subsystem 202 includes a vertical plane gantry 204 configured to rotate about a generally horizontal axis of rotation 206.

Like system 100 described above, system 200 includes an x-ray source 208. The exemplary x-ray source 208 is mounted on, and supported by, a mounting surface 210 of the vertical plane gantry 204. The vertical plane gantry 204 is supported by a bearing 212, and arranged for rotation about the axis of rotation 206. The bearing 212 is, in turn, coupled to and supported by a structural member 214, and the structural member 214 is coupled to and supported by a base member 216 of the vertical plane gantry subsystem 202.

The x-ray source 208 is configured to emit a beam of x-rays 218. The beam of x-rays 218 defines a beam longitudinal axis 220 that, in the illustrated embodiment, intersects (at 222) the axis of rotation 206.

The beam of x-rays 218 will, in respective embodiments, have any of the cross-sections discussed above. Accordingly, in the illustrated example, a cross-section of the beam 218 taken transverse to the longitudinal axis 220 defines a rectangular area of substantially uniform x-ray intensity. This configuration optimizes imaging of the breast while minimizing irradiation of chest wall tissue above the breast. It is implemented, in certain embodiments, by the placement of an x-ray-opaque collimating plate across a portion of an otherwise circular-cross-section beam generated by the x-ray source.

An x-ray detector 224 is also mounted on the mounting surface 210 of the vertical plane gantry 204. In one exemplary embodiment, the x-ray detector 224 includes a flat panel detector having a generally planar receiving surface 226. Receiving surface 226 is disposed generally transverse to longitudinal axis 220 and on the opposite side of axis of rotation 206 from the x-ray source 208.

It will be appreciated by one of skill in the art that the configuration described is merely exemplary of many possible arrangements in which the x-ray source, the x-ray detector, and any other component of the system, may be supported from above, from a side, or in any other way appropriate to achieving the desired function, and that the shape and configuration of the gantry, and of the x-ray detector, will likewise assume any appropriate form in respective embodiments of the invention.

Rotation of the vertical plane gantry 204 about axis of rotation 206 during operation of the imaging system 200 will result in the receiving surface 226 following a transit path 228 about axis of rotation 206. In a typical configuration, the transit path 228 will include at least a portion of a circle disposed transverse to, and centered at, axis of rotation 206. It will be noted, however, that other transit paths are considered to be within the scope of the invention, and to be disclosed herewith.

In the exemplary embodiment illustrated, axis of rotation 206 is disposed in a generally horizontal orientation, and transit path 228 is disposed in a generally vertical plane. Generally, and with reference to further disclosure below, it should be understood that other orientations of the axis of rotation and transit path are considered to fall within the scope of the present disclosure.

In certain embodiments of the invention, one or both of the x-ray source 208 and the x-ray detector 224 are arranged so that their respective positions on the mounting surface 210 of gantry 204 are adjustable. For example, the x-ray source 208 and the x-ray detector 224 may be adjustable in a radial direction (i.e., degree of freedom) with respect to axis of rotation 206, in a circumferential direction (i.e., degree of freedom) with respect to axis of rotation 206, in a direction (i.e., degree of freedom) towards or away from gantry surface 210, or in any other manner deemed beneficial by the designer or user of a particular apparatus embodying the invention.

A patient support subsystem 230 includes a column member 232 and a patient back support portion 234. In the illustrated embodiment, both the vertical plane gantry subsystem 202 and the patient support subsystem 230 are mutually coupled to, and supported by a foundation element 236.

A patient interface panel 238 (otherwise known as a patient table) is disposed between the vertical plane gantry 204 and the patient support subsystem 230. The patient interface panel 238 has a first patient interface surface region 240 and a second distal surface region 242, where the distal surface region 242 is disposed in spaced relation to the patient interface surface region 240.

An internal circumferential edge 244 of the patient interface surface region 240 circumscribes an aperture 246 through the patient interface panel 238 between patient interface surface region 240 and distal surface region 242.

As will be further described below, the patient interface surface region 240 is arranged to segregate the patient from the balance of the vertical plane gantry subsystem 202 with a breast of the patient disposed through the aperture 246. In various embodiments and aspects of the invention, a patient interface subsystem is disposed at the aperture 246. In its various aspects, the patient interface subsystem will provide one or more of an aperture sized and located according to the particular patient and breast being imaged, shielding for regions of the patient that might otherwise be exposed to scattered x-ray photons, and support and stabilization of the breast being imaged, among other features.

In operation, the gantry 204 rotates about axis of rotation 206, carrying x-ray source 208 and x-ray detector 224 in a transit path 228 around the patient's breast. During this transit, x-ray image data is captured by operation of the x-ray detector 224 in conjunction with corresponding interface electronics and computer systems. The x-ray image data corresponds to a plurality of x-ray images taken at respective angular locations about axis of rotation 206. Taken together, the x-ray image data, or a subset of the same, is processed to provide information about the internal state of the breast.

The X-ray detector can be any two dimensional detectors including a flat panel detector, a two dimensional photon counting detector, two dimensional curved detector. To optimize the coverage of breast tissue at chest wall and the patient comfort, the top edge (dead space) of the detector should be minimal (as small as possible). To reduce motion artifacts and improve the sharpness of the reconstruction images, the frame rate of the detector should at least 20 frames/second and at least 512×512 per frame. To obtain an isotropic high spatial resolution of the breast CT system, the cell size of the two dimensional detector should be equal to or smaller than 0.5 mm×0.5 mm/cell.

In the illustrated embodiment, the patient interface panel 238 is coupled to, and supported by, the base member 216 of the vertical plane gantry subsystem 202. In alternative embodiments, the patient interface panel 238 will be coupled to, and supported by, foundation element 236. In additional embodiments of the invention, the patient interface panel 238 will be coupled to and supported by the patient support subsystem 230. In still other embodiments of the invention alternative features of the imaging system 200 will support the patient interface panel 238.

Figure 3:
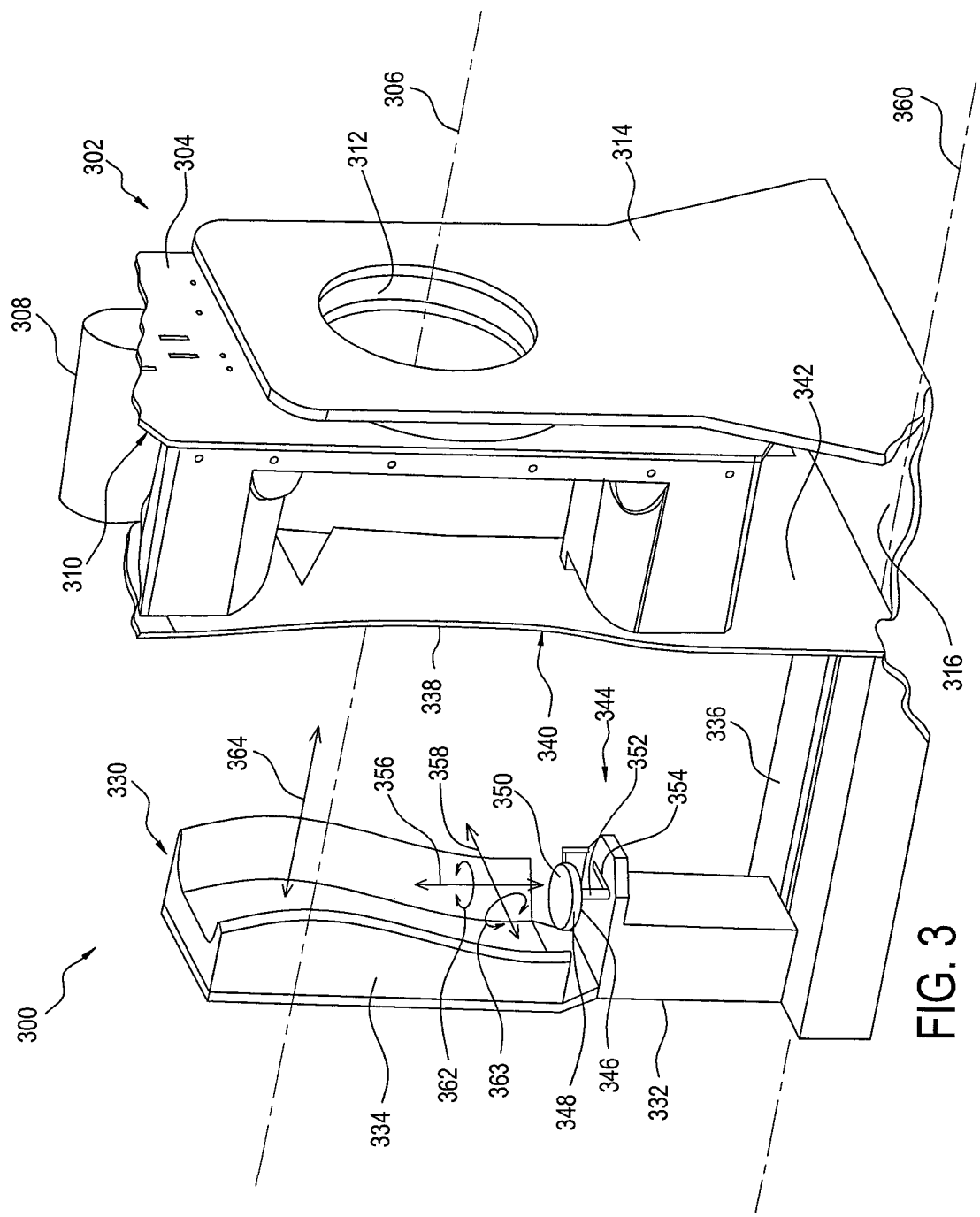
FIG. 3 shows, in schematic perspective view, certain aspects of an exemplary CBBCT imaging system, including a vertical plane gantry subsystem prepared according to principles of the invention.

FIG. 3 shows, in schematic perspective view, a portion of an exemplary CBBCT imaging system 300, including a vertical plane gantry subsystem 302. System 300 illustrates further details of certain embodiments of system 200, and of other embodiments of the invention. The vertical plane gantry subsystem 302 includes a vertical plane gantry 304 configured to rotate about a generally horizontal axis of rotation 306.

Like system 200 described above, system 300 includes an x-ray source 308. The exemplary x-ray source 308 is mounted on, and supported by, a mounting surface 310 of the vertical plane gantry 304. The vertical plane gantry 304 is supported by a bearing 312, and arranged for rotation about the axis of rotation 306. The bearing 312 is, in turn, coupled to and supported by a structural member 314, and the structural member 314 is coupled to and supported by a base member 316 of the vertical plane gantry subsystem 302.

Like system 200, system 300 also includes a patient support subsystem 330. Patient support subsystem 330 includes a column member 332 and a patient back support portion 334. In the illustrated embodiment, both the vertical plane gantry subsystem 302 and the patient support subsystem 330 are mutually coupled to, and supported by a foundation element 336.

A patient interface panel 338 is disposed between the vertical plane gantry 304 and the patient support subsystem 330. The patient interface panel 338 has a first patient interface surface region 340 and a second distal surface region 342, where the distal surface region 342 is disposed in spaced relation to the patient interface surface region 340.

Patient support subsystem 330 also includes an exemplary seat apparatus 344. In the illustrated embodiment, exemplary seat apparatus 344 is coupled to, and supported by, column member 332. The seat apparatus 344 includes a saddle portion 346 with a structural body member 348 and a saddle upper surface region 350. Saddle upper surface region 350 is adapted to position and support a patient sitting astride the saddle portion 346 during imaging as well as during optional supplemental procedures.

In the illustrated embodiment, structural body member 348 is substantially fixedly coupled to an upper end of an exemplary seat column 352 which, in the illustrated embodiment, is disposed through an aperture or slot 354 into the column member 332.

In certain embodiments of the invention, a lower end of the exemplary seat column 352 is operatively coupled to a seat adjustment mechanism. The seat adjustment mechanism is disposed within a cavity or recess within the column member 332 and coupled to the column member for support. Accordingly, the weight of a patient seated on the saddle upper surface region 350 is transferred through the structural body member 348 of the saddle to the seat column 352, and from there through the seat adjustment mechanism to the column member 332.

As discussed above, column member 332 is supported by foundation element 336. Therefore, the weight of the patient is ultimately supported by the foundation element 336 and transferred through the foundation element 336 to a floor supporting the CBBCT imaging system 300.

In a desirable aspect of certain embodiments of the invention, the seat adjustment mechanism permits positional adjustment of the saddle 346 vertically 356 and transverse 358 to a longitudinal axis 360 of the foundation element 336. In certain embodiments, the seat adjustment mechanism also permits pivotal rotations in additional degrees of freedom, i.e., yaw 362 and pitch 363 of the saddle. These various adjustments will improve the comfort and optimal positioning of the patient.

In a still further aspect of the invention, in certain embodiments the saddle will be retractable (e.g., into a cavity or recess within the column member) or foldable, or otherwise removable so that a patient being imaged will not sit on the saddle, but will stand on an upper surface of the foundation element 336, or on a patient platform coupled to the foundation element 336 or column member 332. Accordingly, seating on the saddle will be available where desirable, but the saddle need not be employed where a standing mode of patient support is preferable.

In still further embodiments of the invention, the saddle portion will not be coupled to the patient support subsystem, but will be coupled to a surface region of the patient interface panel 338 in the manner generally described below with respect to CBBCT imaging system 1500 of FIG. 15.

As will be appreciated by one of skill in the art, both the saddle portion 346, and the patient back support portion 334 will, be shaped and configured to promote optimal comfort and positioning of the patient with respect to the vertical plane gantry subsystem 302. In certain embodiments, the saddle portion 346 and the patient back support portion 334 will include materials that advantageously are biocompatible and exhibit desirable characteristics of rheology and elastic durometer.

Accordingly, in respective embodiments of the invention, the saddle portion 346 and patient back support portion 334 will include materials appropriate to achieve these ends. Such materials will include, merely for example and without limitation, various copolymers or block copolymers (Kratons®) available from Kraton Polymers such as styrene-butadiene rubber or styrene-isoprene rubber, EPDM (ethylene propylene diene monomer) rubber, nitrile (acrylonitrile butadiene) rubber, polyurethane, polybutadiene, polyisobutylene, neoprene, natural latex rubber and the like. Foam materials may be closed cell foams or open cell foams, and may include, but is not limited to, a polyolefin foam such as a polyethylene foam, a polypropylene foam, and a polybutylene foam; a polystyrene foam; a polyurethane foam; any elastomeric foam made from any elastomeric or rubber material mentioned above; or any biodegradable or biocompostable polyesters such as a polylactic acid resin (comprising L-lactic acid and D-lactic acid) and polyglycolic acid (PGA); polyhydroxyvalerate/hydroxybutyrate resin (PHBV) (copolymer of 3-hydroxy butyric acid and 3-hydroxy pentanoic acid (3-hydroxy valeric acid) and polyhydroxyalkanoate (PHA) copolymers; and polyester/urethane resin. One of skill in the art will appreciate that the foregoing are merely exemplary of a wide variety of possibilities that would be applied in appropriate applications of the invention.

Additionally, certain aspects of the invention, as expressed in corresponding embodiments, will include an active back support mechanism coupled between the patient back support portion 334 and, for example, column member 332. In certain embodiments, the active back support mechanism will permit adjustment of the position and orientation of the patient back support 334 in additional degrees of freedom, i.e., pitch, roll and yaw, as well as linear positioning with respect to the saddle in direction 364. In other embodiments, and as will be further discussed below, the active back support mechanism will include a bladder or expandable cushion that when activated, serves to urge the patient towards the patient interface surface region 340 of the patient interface panel 338.

In a further aspect of the invention, foundation element 336 includes a linear bearing device. The linear bearing device is coupled between base element 316 of the vertical plane gantry subsystem 302 and foundation element 336 of the CBBCT imaging system 300. Accordingly, the position of the vertical plane gantry subsystem 302 with respect to the patient support subsystem 330 is adjustable along direction 364.

This adjustability allows a patient to mount the patient support subsystem 330 and be placed in position for scanning with the vertical plane gantry subsystem 302 positioned relatively distal to the patient support subsystem 330. Thereafter, and as will be further described below, the vertical plane gantry subsystem 302 can be adjusted into proximity with the patient for effective scanning.

In certain embodiments of the invention, this adjustment is achieved by manual displacement of the vertical plane gantry subsystem 302. In other embodiments of the invention, lateral adjustment of the position of the vertical plane gantry subsystem 302 is controlled by a linear actuator.

In various embodiments of the invention, the linear actuator includes an electric motor that, by its operation, tends to effect shortening and lengthening of the linear actuator. One of skill in the art will appreciate, however, that any number of linear actuators, rotary actuators, or other operative mechanisms and arrangements will be employed in corresponding embodiments of the invention.

Thus for example, in certain embodiments of the invention, the linear actuator will include one or more of an electrical solenoid, a pneumatic cylinder, a hydraulic cylinder, a pneumatic bladder, a hydraulic bladder, a linear electric motor, a rotary electric motor, an Acme screw and nut, a lead screw, a ballscrew, a cable, a pulley, a timing belt, a timing pulley, an appropriately sized worm gear reducer, a rack and pinion assembly, a rack and worm gear assembly, and any other appropriately functioning actuator component that is known or becomes known in the art.

Figure 4A:
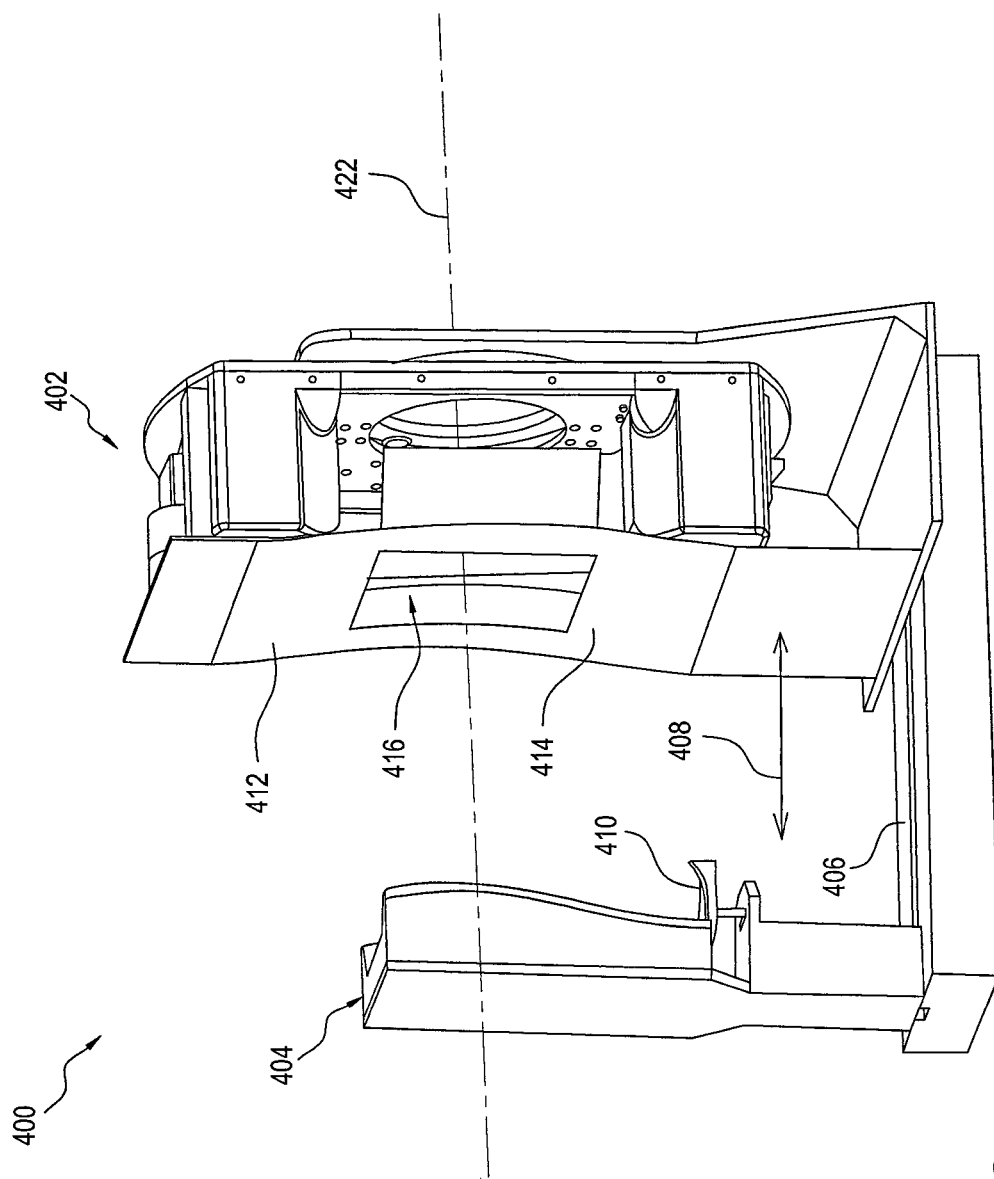
FIG. 4A shows, in schematic perspective view, aspects of an exemplary CBBCT imaging system prepared according to principles of the invention.
Figure 4B:
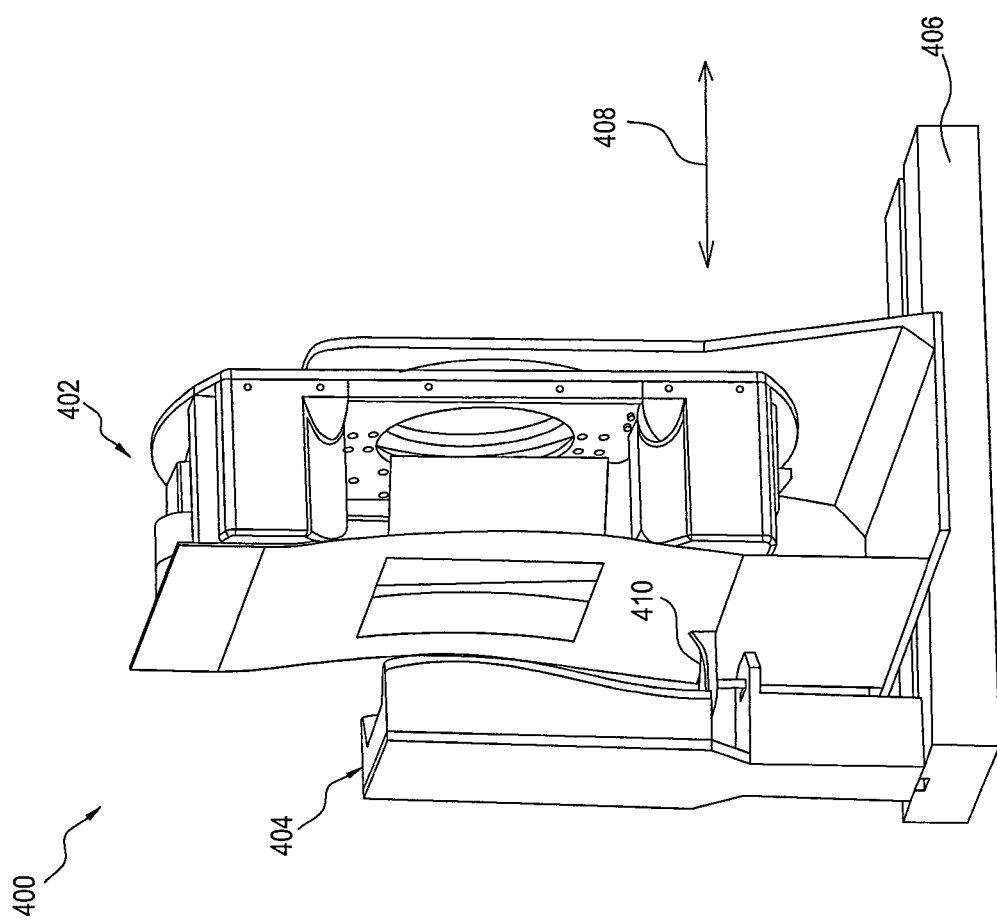
FIG. 4B shows, in schematic perspective view, additional aspects of an exemplary CBBCT imaging system prepared according to principles of the invention.
Figure 4C:
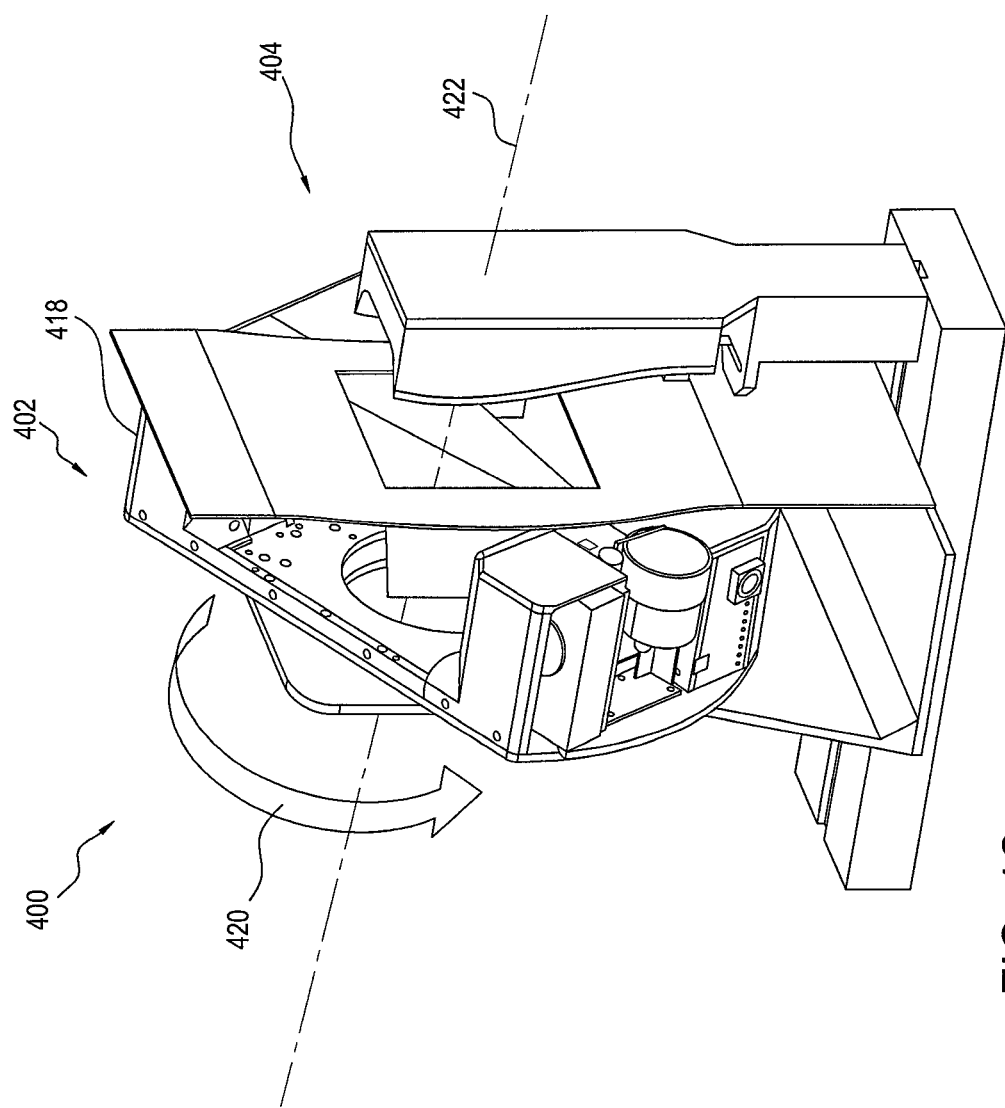
FIG. 4C shows, in schematic perspective view, still further aspects and operations of an exemplary CBBCT imaging system prepared according to principles of the invention.
Figure 4D:
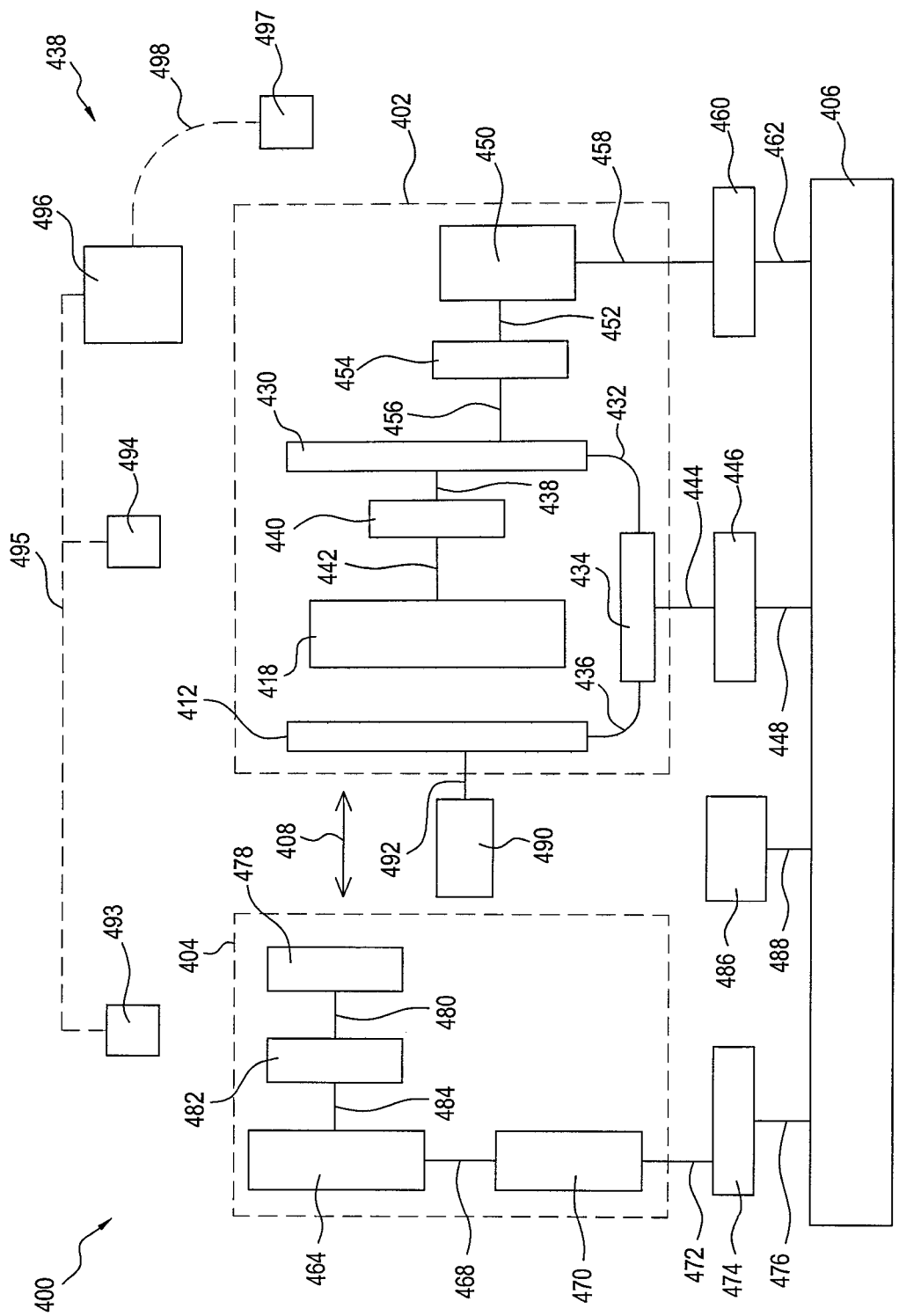
FIG. 4D shows, in schematic block diagram form, further aspects of a CBBCT imaging system including exemplary safety features prepared according to principles of the invention.

FIG. 4A-4D show operational aspects and methods of a CBBCT imaging system 400 similar to systems 200 and 300 described above. FIGS. 4A and 4B show loading and operation configurations respectively of the imaging system 400. FIG. 4C illustrates operation of the vertical plane gantry subsystem according to an example of the invention. FIG. 4D shows relational and safety features of the imaging system 400.

In FIG. 4A the CBBCT imaging system 400 includes a vertical plane gantry subsystem 402 and a patient support subsystem 404. The vertical plane gantry subsystem 402 and the patient support subsystem 404 are mutually coupled to a foundation element 406.

In certain aspects of the invention, as expressed in respective embodiments, the patient support subsystem 404 is substantially fixedly coupled to the foundation element 406, whereas the vertical plane gantry subsystem 402 is movably coupled to the foundation element 406. In the illustrated embodiment, for example, the vertical plane gantry subsystem 402 is adapted to be adjusted towards and away from the patient support subsystem 404 along direction (i.e., degree of freedom) 408.

It will be appreciated by the reader that, although the present description relates to a system in which the patient support subsystem 404 is substantially fixedly coupled to the foundation element 406 and the vertical plane gantry system 402 is movable relative to the same, in alternative embodiments, the reverse will be true. That is, in certain embodiments, the vertical plane gantry system 402 will be substantially fixedly coupled to the foundation element 406, while the patient support subsystem 404 will be movable. In still other embodiments, both the patient support subsystem 404 and the vertical plane gantry subsystem 402 will be movable—these examples illustrating an adjustability of the distance in direction 408 between the two elements.

In FIG. 4A the CBBCT system 400 is shown in a first state in which the vertical plane gantry subsystem 402 is disposed relatively distant from the patient support subsystem 404.

FIG. 4B shows, in schematic perspective view, further aspects of exemplary CBBCT imaging system 400. In FIG. 4B the CBBCT system 400 is shown in a second state in which the vertical plane gantry subsystem 402 is disposed relatively proximate to the patient support subsystem 404.

Referring again to FIG. 4A, consistent with the description above in relation to systems 200 and 300, the patient support subsystem 404 of the CBBCT system 400 includes an adjustable saddle 410 and a patient interface panel 412.

In typical operation, the CBBCT system 400 is placed in an initial first state (i.e., as shown in FIG. 4A) in preparation for receiving a patient. The relatively large distance between the vertical plane gantry subsystem 402 and the patient support subsystem 404 allows the patient to easily access and mount the saddle 410.

In certain embodiments of the invention the height and other positional parameters of the saddle 410, and of the patient support subsystem 404 as a whole, are adjusted prior to entry of the patient into the system. In alternative embodiments of the invention, adjustments of the saddle 410 will be made after the patient is positioned on the saddle. In still further aspects and embodiments of the invention, adjustments are made to the parameters of the patient support subsystem both before and after the patient is disposed on the saddle 410.

Once the patient is positioned, the system is adjusted to reduce the relative distance between the patient and the patient interface panel 412 of the system. Accordingly, in certain embodiments of the invention, the vertical plane gantry subsystem 402 is moved towards the seated patient along dimension 408 until a patient contact surface region 414 of the patient interface panel 412 is disposed in close proximity to the patient.

This disposes the patient in contact with a portion of the patient contact surface region 414 of the patient interface panel 412, and a breast of the patient that is to be imaged is disposed through the aperture 416.

As will be further discussed below, in various aspects and embodiments of the invention, a patient interface subpanel will be disposed at the aperture (see, e.g., patient interface subpanel 710 described below), such that the patient will be in contact with a surface region of the subpanel, and the breast to be imaged will be disposed through an aperture of the subpanel.

Once the patient is positioned as described above, the patient and/or technical and medical personnel can make further adjustments to the positioning of the breast and any other procedural preparations required prior to imaging. Thereafter, CBBCT imaging can proceed.

FIG. 4C shows exemplary CBBCT imaging system 400 with imaging underway. In FIG. 4B the CBBCT system 400 is shown in the second state, with the vertical plane gantry subsystem 402 disposed relatively proximate to the patient support subsystem 404. An imaging scan is underway, and the vertical plane gantry 418 is shown in rotation 420 about an axis of rotation 422.

FIG. 4D shows, in schematic block diagram form, further aspects of a CBBCT imaging system 400 including exemplary safety features thereof. With further reference to the description above, in CBBCT systems 300 and 400 the vertical plane gantry subsystem 402 is adjustable towards and away from the patient support subsystem 404 along foundation element 406 in direction 408. One of skill in the art will appreciate that this motion must be limited to ensure the safety of the patient when disposed between the patient support subsystem 404 and the vertical plane gantry subsystem 402.

The CBBCT imaging system, in its various embodiments will therefore include interlock apparatus and safety release/breakaway mechanisms. These mechanisms will ensure that a minimum distance and maximum pressure applied between the vertical plane gantry subsystem 402 and the patient support subsystem 404 will be limited to defined and repeatable values. Moreover, in a typical system, an emergency stop/release subsystem 438 will be provided to arrest motion of the subsystems and release any pressure applied.

As discussed above, the vertical plane gantry subsystem 402 includes a structural member 430. The structural member 430 is coupled to 432 and supported by a base member 434. The patient interface panel 412 is also coupled to 436 and supported by the base member 434. The structural member 430 is also coupled to 438 and supports a rotary bearing 440, and the rotary bearing 440 is coupled to 442 and supports the vertical plane gantry 418 for rotation about the rotary axis of the bearing.

The base element 434 is also coupled 444 to, and supported by, a linear bearing 446. The linear bearing 446 is coupled to 448, and supported by the foundation element 406. Accordingly, the foundation element 406 supports the vertical plane gantry subsystem 402 in sliding motion in direction 408.

This motion is motivated by a linear actuator 450. In light of the present discussion, and in order to ensure the safety of the patient the linear actuator 450 is coupled to the structural member (and accordingly the patient interface panel) through an exemplary safety feature. Accordingly, linear actuator 450 is coupled to 452 a first force limiting clutch 454 which is, in turn, coupled to 456 the structural member 430. In certain embodiments of the invention, the linear actuator 450 is also coupled to 458 a second force limiting clutch 460. The second force limiting clutch 460 is coupled to 462 the foundation element 406.

When the first 454 and second 460 force limiting clutches are engaged, the linear actuator 450 is operative to move the structural member 430, and consequently the patient interface panel 412 with respect to the foundation element 406. If either the first 454 or second 460 force limiting clutch disengages, however, the structural member 430, and the balance of the vertical plane gantry subsystem 402 is released from the foundation element 406 with respect to motion in direction 408.

Accordingly, if either of the force limiting clutches 454, 460 is disengaged, the patient interface panel 412 will no longer advance towards the patient along direction 408 and, preferably, the patient (and/or any medical/technical personnel) will be able to urge the patient interface panel 412 away from the patient by pushing on it.

The illustrated patient support subsystem 404 also includes exemplary safety features. Patient support subsystem 404 includes a patient back support portion 464 coupled to 468 and supported by a column member 470. The column member 470 is, in turn, coupled to 472 a force limiting clutch apparatus 474 including a third force limiting clutch. The force limiting clutch apparatus 474 is coupled to 476 the foundation element 406.

As will be readily appreciated by one of skill in the art, when the force limiting clutch apparatus 474 is engaged, the column member 470 (and therefore the patient back support portion 464) is substantially fixedly coupled to the foundation element 406 with respect to motion in direction 408. When desirable (i.e. in order to ensure patient comfort and safety) the clutch apparatus 474 releases. This permits motion, with respect to foundation element 406, of the column member 470 and patient back support portion 464 away from the patient interface panel 412 in direction 408.

Accordingly, if the force limiting clutch apparatus 474 is disengaged, the patient support subsystem 404 will no longer be fixedly coupled to the foundation element 406 against the advancement along direction 408 of the patient interface panel 412. Therefore, the patient (and/or any medical/technical personnel) will be able to urge the patient support subsystem 404 away from the vertical plane gantry subsystem 402 by, for example, pushing against the patient interface panel 412.

One of skill in the art will understand that the force limiting clutch apparatus 474 will, in certain embodiments, include a linear bearing. The linear bearing will facilitate motion in direction 408 of the patient support subsystem 404 with respect to foundation element 406 once the force limiting clutch apparatus 474 has been released.

In other embodiments of the invention, a release of the force limiting clutch apparatus 474 will permit a pivotal motion of the patient support subsystem 404 with respect to foundation element 406, and away from the vertical plane gantry subsystem 402. In such an exemplary embodiment, for example, the force limiting clutch apparatus 474 will include a mechanical hinge, an axle, a linkage assembly, a living polymer hinge or other device appropriate to the desired pivotal motion.

In certain embodiments of the invention, the force limiting clutch apparatus 474 will include a helper mechanism that motivates or assists the motion of the patient support subsystem 404 in direction 408 away from the vertical plane gantry subsystem 402. In this way, a patient that lacks sufficient strength to push the two subsystems apart from one another will still be protected in the event that the force limiting clutch apparatus 474 is released. Likewise, in certain embodiments, a helper mechanism will be provided that assists the motion of the vertical plane gantry subsystem 402 in direction 408 away from the patient support subsystem 404.

In light of the foregoing, one of skill in the art will understand that the invention includes any of a wide variety of passive or active helper mechanisms appropriate to the requirements of a particular embodiment, and implement the same with a minimum of experimentation. Thus, in certain embodiments of the invention, the helper mechanism will include any of an pneumatic cylinder, a pneumatic bladder, a pressurized gas reservoir, a gas generator (e.g., an explosive gas generator), a hydraulic cylinder, a hydraulic bladder, a hydraulic fluid reservoir, a hydraulic pump, a spring such as, for example, a helical compression spring, a helical tension spring, a spiral spring, a torsion spring, any of the linear actuators and related assemblies suggested above, whether used alone or in combination, and any other appropriate mechanism that is known or becomes known in the art.

As illustrated, the patient support subsystem 404 also includes an active back support mechanism 478 (as described above, for example, in relation to FIG. 3) operatively coupled to 480 a safety device 482 which is, in turn, operatively coupled to 484 the back support portion 464.

Consistent with the discussion above, the safety device 482 will, when desired, release pressure that otherwise urges the patient against the patient interface panel 412. Accordingly, in respective embodiments, the safety device 482 will include a force limiting clutch, a safety valve limited bladder, or other apparatus or device appropriate to this purpose.

One of skill in the art will also appreciate that any of the force limiting clutches described above may include one or more of, for example, a mechanical friction clutch, a magnetic clutch, a pressure release safety valve in combination with a cylinder or bladder, a frangible element such as a frangible metal element, a frangible polymer element, a frangible glass element, a crushable element such as, for example, a crushable foam polymer element, a malleable or ductile metallic bellows or other malleable or ductile metallic element disposed in compression or tension, a ratchet and pawl assembly, or any other device or apparatus configured and adapted to release, whether once or repeatedly, under a predictable amount of force. It will be understood that, in respective embodiments, the force limiting clutch may include disposable and non-disposable (i.e., reusable) components. For example, a frangible element may be a one time use/disposable element that is replaced in the event that the clutch is released.

In certain embodiments of the invention, the safety features of CBBCT imaging system 400 will include one or more mechanical stops. The mechanical stops will provide mechanical interference between elements of the system that prevent any motion of the system elements into a state that is dangerous or uncomfortable to the patient.

Thus, for example, mechanical stop 486 is operatively coupled 488 to foundation element 406. The mechanical stop 486 is positioned to limit a motion of the vertical plane gantry subsystem 402 in direction 408 with respect to foundation element 406, and therefore with respect to the patient support subsystem 404.

In certain embodiments of the invention, the mechanical stop 486 is substantially permanently coupled to foundation element 406. In other embodiments of the invention, the mechanical stop 486 is substantially fixedly, but releasably, coupled to the foundation element 406. Accordingly, the location of the mechanical stop 486 with respect to the foundation element 406 is adjustable according to the requirements of a particular patient or procedure.

In a further aspect or embodiment of the invention, a further mechanical stop 490 is operatively coupled to 492 the patient interface panel 412. Like mechanical stop 486, the mechanical stop 490 is effective to limit the respective distance between the vertical plane gantry subsystem 402 and the patient support subsystem 404 to no less than a minimum distance. Like mechanical stop 486, mechanical stop 490 may be substantially permanent, or maybe removable and/or replaceable, with a variety of different mechanical stops of corresponding length. Accordingly, the length of certain mechanical stops 490 will be selected or adjusted according to the requirements of a particular patient or procedure. A kit of mechanical stops 490 of various sizes may be provided with a particular embodiment of the invention.

In certain embodiments of the invention, the safety features of CBBCT imaging system 400 will include one or more emergency stop/release subsystems 438 to arrest motion of the vertical plane gantry and patient support subsystems and release any pressure applied.

In the illustrated embodiment, the emergency stop subsystem 438 includes a plurality of patient accessible stop buttons (or other actuators) e.g., 493, 494 coupled respectively to the vertical plane gantry subsystem 402, and/or the patient support subsystem 404. The patient accessible stop buttons are signalingly coupled to 495 a control system 496. One of skill in the art will understand that the control system will be, for example, a pneumatic control system, electronic control system including, e.g., a microcontroller and related elements known in the art, an electromechanical control system including, for example, relays solenoids and power supplies as known in the art, and any other control components appropriate to the requirements of the system that are known or become known in the art.

As illustrated, additional stop buttons, e.g. 497, will be provided in locations accessible to technical and/or medical personnel, and operatively coupled 498 to the control system 496, to ensure that any of the patient and technical and/or medical personnel will be able to immediately arrest motion of the subsystems and release the patient from the CBBCT imaging system 400. Likewise, one of ordinary skill in the art will immediately understand that the control system 496 will be operatively coupled to one or more of the linear actuator 450, the active back support mechanism 478, and any of the safety devices 454, 460, 474, 482, etc. present in the CBBCT imaging system 400 to control the same and ensure patient safety and comfort.

Figure 5:
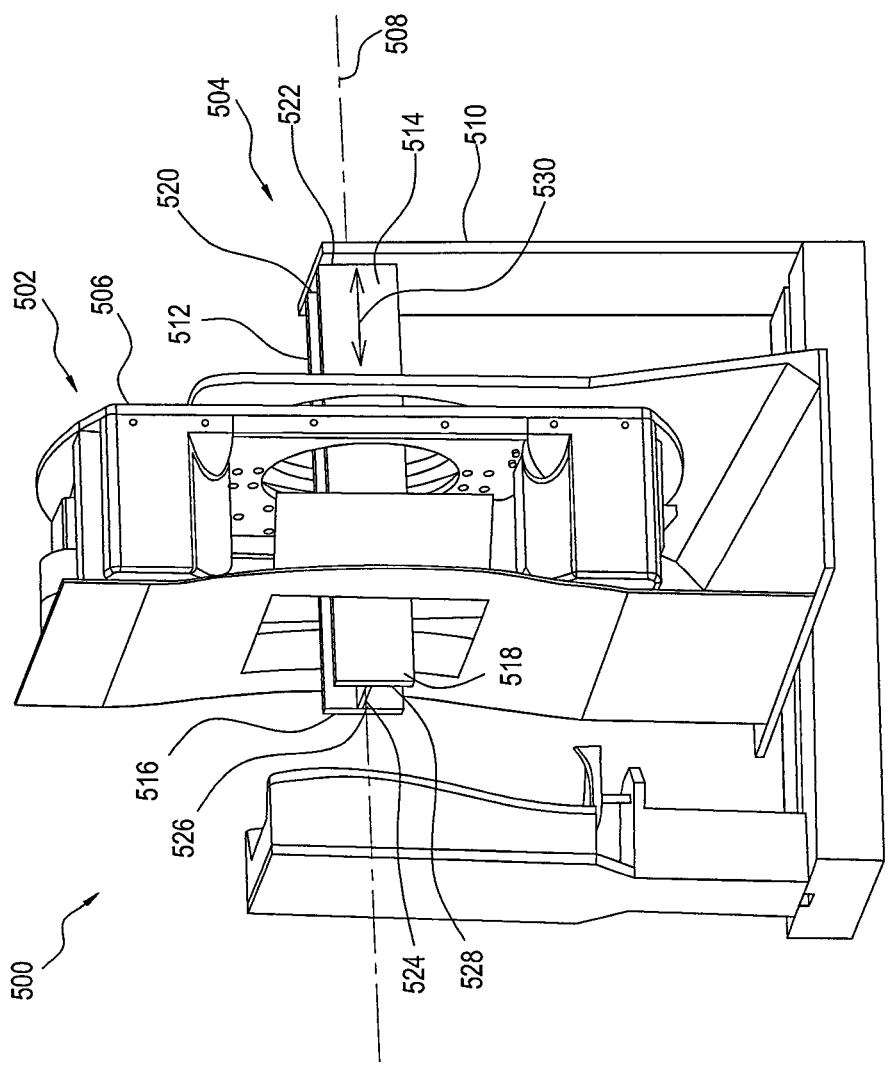
FIG. 5 shows, in schematic perspective view, a portion of an exemplary CBBCT imaging system, including a coaxial support subsystem prepared according to principles of the invention.

FIG. 5 shows, in schematic perspective view, a portion of an exemplary CBBCT imaging system 500, including a vertical plane gantry subsystem 502 and a coaxial support subsystem 504. System 500 illustrates further details of certain embodiments of systems 200, 300 and 400, and of other embodiments of the invention. The vertical plane gantry subsystem 502 includes a vertical plane gantry 506 configured to rotate about a generally horizontal axis of rotation 508.

The exemplary coaxial support subsystem 504 includes a vertical column structural member 510 and first, 512 and second 514 horizontal structural members. The horizontal structural members 512, 514 have respective proximal ends 516, 518 and respective distal ends 520, 522. The horizontal structural members 510, 512 are operatively coupled to the vertical column structural member 510 at their respective distal ends 520, 522. Accordingly, the horizontal structural members 510, 512 are configured and adapted to support and stabilize ancillary subsystems of the CBBCT imaging system.

It will be noted that the illustrated horizontal structural members 512, 514 are disposed in a cantilevered configuration, supported by vertical column structural member 510. It will be appreciated by one of skill in the art, however, that any of a wide variety of support arrangements will be effective in respective embodiments of the invention to achieve at least the objective of providing support to the horizontal structural members 512, 514.

One of skill in the art will appreciate that the arrangement described here, including two horizontal structural members 512, 514, is merely exemplary of a wide variety of arrangements including, for example a single structural member, solid members including I-beams or any other configuration of solid member, tubular beams including circular cylindrical tubular beams, box beams, and trusses formed of a plurality of solid or tubular members, etc., all of the foregoing (as well as any comparable element known, or that becomes known in the art), being intended to fall within the current disclosure.

According to the exemplary embodiment of the invention illustrated, the coaxial support subsystem 504 includes a coupling device 524. Respective first 526 and second 528 linear bearing devices are coupled to the first and second horizontal structural members 510, 512 respectively and mutually coupled to the coupling device 524.

In various aspects and embodiments of the invention, the coaxial support subsystem 504 will support any of a wide variety of ancillary equipment including, for example, a breast stabilization unit, a stationary scan subsystem, an x-ray filter subsystem and elements, and x-ray grating subsystem and elements, ancillary cameras and other imaging equipment, or other ancillary equipment that is known or becomes known in the art and is effective to cooperate with the balance of the CBBCT imaging system.

Accordingly, any of the foregoing ancillary equipment will be coupled to the coupling device 524, and therefore operatively supported by the horizontal structural members, 512, 514. One of skill in the art will appreciate that the presence of the linear bearings 526, 528 permits positional displacement of the ancillary equipment in a manner that allows the ancillary equipment to be moved from a storage configuration, located at the distal end e.g., 520, 522 of the horizontal structural members 512, 514 to an operative configuration at the proximal ends 516, 518 of the horizontal structural members.

In certain embodiments, displacement of the coupling device 524 backward and forward along dimension 530 between the distal storage configuration and the proximal operative configuration described above will be effected manually. In certain further aspects of the invention, the coaxial support subsystem 504 will include a linear actuator coupled between coupling device 524 and the balance of the coaxial support system 504 (e.g., one or more of the horizontal structural members 512, 514 or the vertical column structural member 510). The linear actuator will be effective to actuate and control the motion of the coupling device 524 (and ancillary equipment) backward and forward along dimension 530 between the distal storage configuration and the proximal operative configuration described above.

In certain embodiments of the invention, the linear actuator will be under manual control. In other embodiments of the invention, the linear actuator will be automatically controlled directly or indirectly by a system computer, or directly or indirectly by dedicated embedded hardware such as, for example, a dedicated microcontroller.

As will be appreciated by one of skill in the art, the herewith-described linear actuator (and any of the linear actuators referenced herewith) can be implemented with a wide variety of actuators available in the art. For example, in certain embodiments, the linear actuator will include one or more of a rack and pinion apparatus, an Acme screw and Acme nut; a ballscrew apparatus; a linear stepping motor; a transverse complementary ramps; a pneumatic cylinder; a pneumatic bladder; a pneumatic bellows; a hydraulic cylinder; a hydraulic bladder; a hydraulic bellows; a scissors linkage mechanism, including, for example, a scissors linkage mechanism linkage operated by a lead screw, a cylinder, or any of the other actuators discussed herewith, or any other appropriate actuator; a sarrus linkage mechanism; a thermoelectric actuator; a shape memory alloy actuator; a cable and pulley arrangement; as well as any of a wide variety of manual actuators such as, for example, a handcrank and/or a ratchet lever; a compressive spring; a tension spring; a torsion spring; an assembly of leaf springs; a spring including a plurality of Belleville washers; or any other linear actuator currently known, or that becomes known in the art, that is suited to the requirements of a particular application and to providing the requisite extension function.

Thus for example, in certain embodiments of the invention, the linear actuator will include one or more of an electrical solenoid, a pneumatic cylinder, hydraulic cylinder, a pneumatic bladder, a hydraulic bladder, a linear electric motor, linear stepping motor, a rotary actuator along with: an Acme screw and nut, a lead screw, a ballscrew, a cable, a pulley, a timing belt, a timing pulley, an appropriately sized worm gear reducer, a rack and pinion assembly, a rack and worm gear assembly, a piezoelectric actuator, a piezoelectric actuator combined with a ratchet and pawl driver, a spring loaded actuator, and actuator including a shape metal alloy, and any other appropriately functioning actuator component that is known or becomes known in the art.

In certain embodiments, one or more units of ancillary equipment will be removably coupled to the coupling device, such that a particular ancillary equipment unit can be installed to the coupling device according to the requirements of a particular patient and of a particular imaging/diagnostic protocol. Further, in respective embodiments of the invention, installation and removal of the ancillary equipment from the coupling device will be effected manually, or automatically by a corresponding motion control system.

In certain embodiments of the invention, one or more diagnostic equipment units will be stored in a cartridge or magazine that is adapted to be permanently or temporarily fixed to the CBBCT imaging system 500. Accordingly, the above-described motion control system will retrieve a required ancillary equipment unit from the cartridge or magazine and install the same to the coupling device according to the requirements of a particular patient or imaging/diagnostic protocol.

Figure 6A:
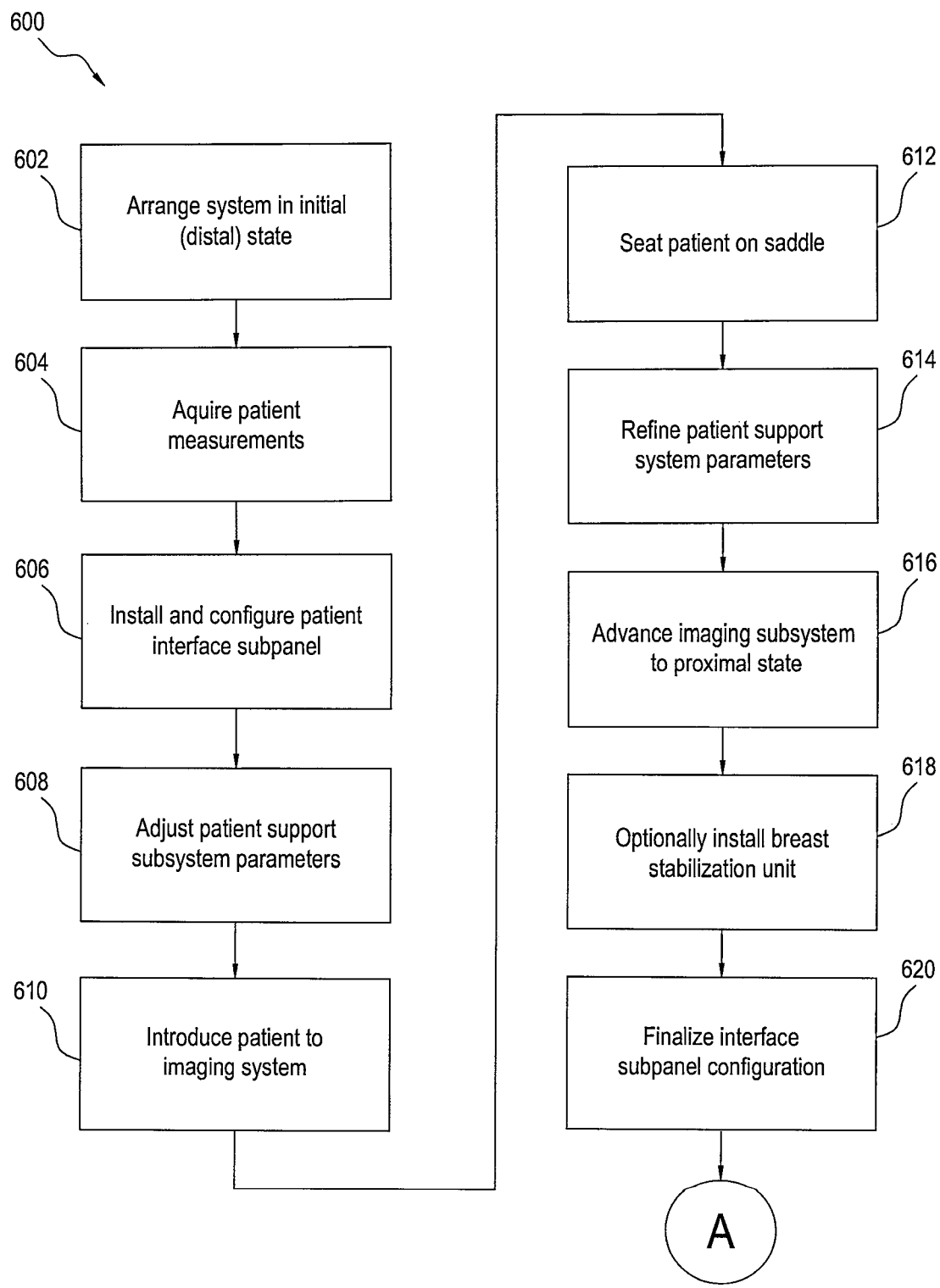
FIG. 6A shows, in functional block diagram form, certain aspects of processes and methods for using a CBBCT imaging system prepared according to principles of the invention.
Figure 6B:
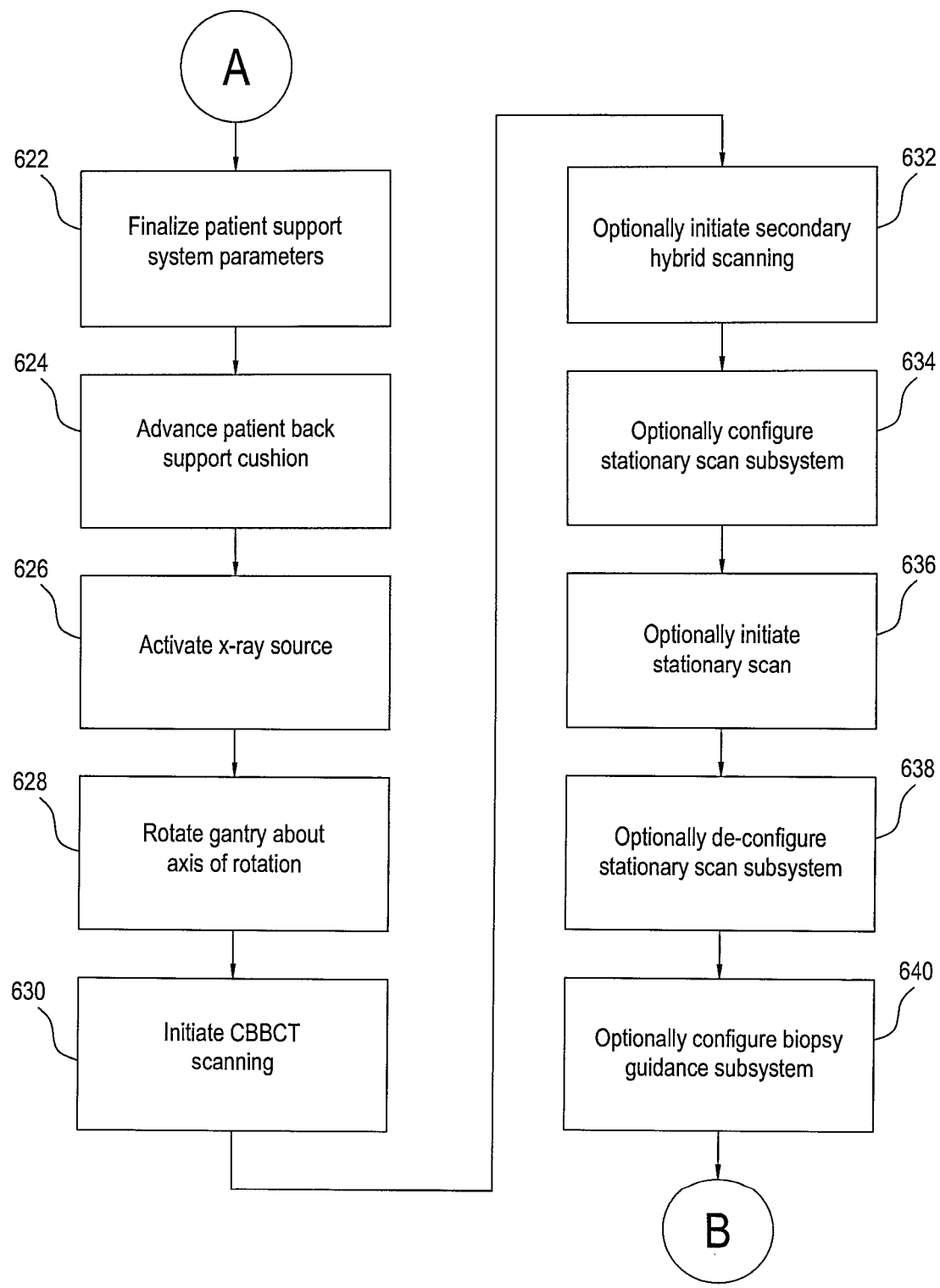
FIG. 6B shows, in functional block diagram form, further aspects of processes and methods for using a CBBCT imaging system prepared according to principles of the invention.
Figure 6C:
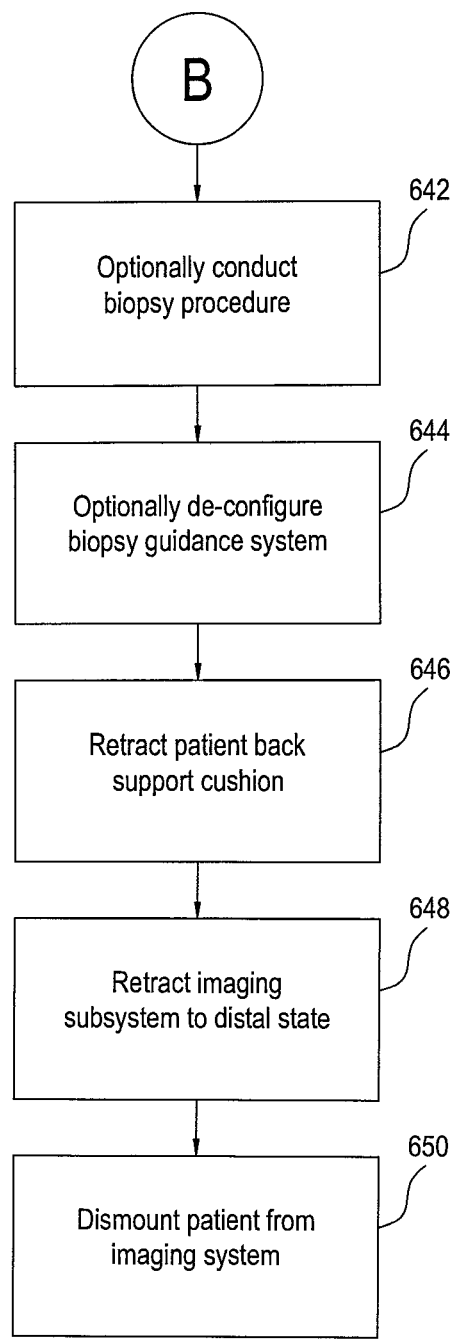
FIG. 6C shows, in functional block diagram form, additional aspects of processes and methods for using a CBBCT imaging system prepared according to principles of the invention.

FIGS. 6A-6C show, in functional block diagram form, processes and methods 600 for using a CBBCT imaging system according to principles of the invention. One of skill in the art will appreciate that the methods described herewith will be effectively employed along with any of the above-describe systems 200, 300, 400, 500, and with additional imaging systems.

Accordingly, FIG. 6A illustrates the steps of arranging 602 a CBBCT imaging system in an initial (distal) state; capturing 604 patient measurements (i.e. body dimensions and characteristics); installing and configuring 606 a patient interface subpanel; making preliminary adjustments 608 of patient support system parameters; introducing 610 a patient to imaging system; seating 612 the patient the saddle; further adjusting 614 the patient support system parameters to ensure patient comfort and optimal imaging position; advancing 616 the imaging subsystem towards the patient so that the imaging subsystem (i.e., the vertical plane gantry subsystem) moves into the secondary (proximal) state described above; adjusting the configuration 618 of the patient interface subpanel including, for example, optionally installing a breast stabilization unit; finalize patient interface subpanel configuration 620; further adjusting 622 the patient support system parameters to improve patient positioning for comfort and imaging; advancing 624 the patient back support cushion towards the back of the patient so as to urge the patient against the patient interface panel, and stabilize the patient against inadvertent movement; activating 626 the x-ray source; rotating 628 the gantry about axis of rotation; and initiating 630 CBBCT scanning.

In addition to the steps indicated above, the methods and processes 600 will optionally include any one or more of the steps of: optionally initiating 632 secondary hybrid scanning such as, for example and without limitation, CBBCT/ultrasonic hybrid scanning, CBBCT/PET hybrid scanning, CBBCT/terahertz hybrid scanning, CBBCT/optical hybrid scanning; optionally configuring 634 a stationary scan subsystem and initiating 636 a stationary scan, as well as optionally de-configuring 638 the stationary scan subsystem; optionally configuring 640 a biopsy guidance subsystem for guiding manual biopsy procedures, optionally conducting 642 a biopsy procedure, and optionally de-configuring 644 the biopsy guidance system (or the same with respect to automatic biopsy procedures). Of course one of skill in the art, having the benefit of the present disclosure will, in hindsight, appreciate that other optional steps combining available ancillary equipment and methods with the present method will be desirable and readily implemented. All of the foregoing are, therefore, intended to be within the scope of the present disclosure.

The disclosed methods and processes further include the steps of retracting 646 the patient back support cushion; retracting 648 the imaging subsystem away from the patient into the initial (distal) state; and dismounting 650 the patient from imaging system.

Referring again to FIG. 2, the illustrated embodiment shows a patient interface panel 238 disposed between the rotating gantry 204 and the patient support subsystem 230. The patient interface panel 238 has a first patient interface surface region 240 and a second distal surface region 242, where the distal surface region 242 is disposed in spaced relation to the patient interface surface region 240.

The internal circumferential edge 244 of the patient interface surface region 240 circumscribes an aperture 246 through the patient interface panel 238 between patient interface surface region 240 and distal surface region 242.

As initially discussed above, the patient interface surface region 240 is arranged to segregate the patient from the balance of the vertical gantry subsystem 206 with a breast of the patient disposed through the aperture 246. In various embodiments and aspects of the invention, a patient interface subpanel is disposed at the aperture 246. In its various aspects, the subpanel will provide one or more of an aperture sized and located according to the characteristics of the particular patient and breast being imaged, shielding for regions of the patient that might otherwise be exposed to scattered x-ray photons, fixturing features for mounting in support of ancillary equipment, and support and stabilization of the breast being imaged, among other features. Further aspects and details of the subpanel are now provided.

Figure 7:
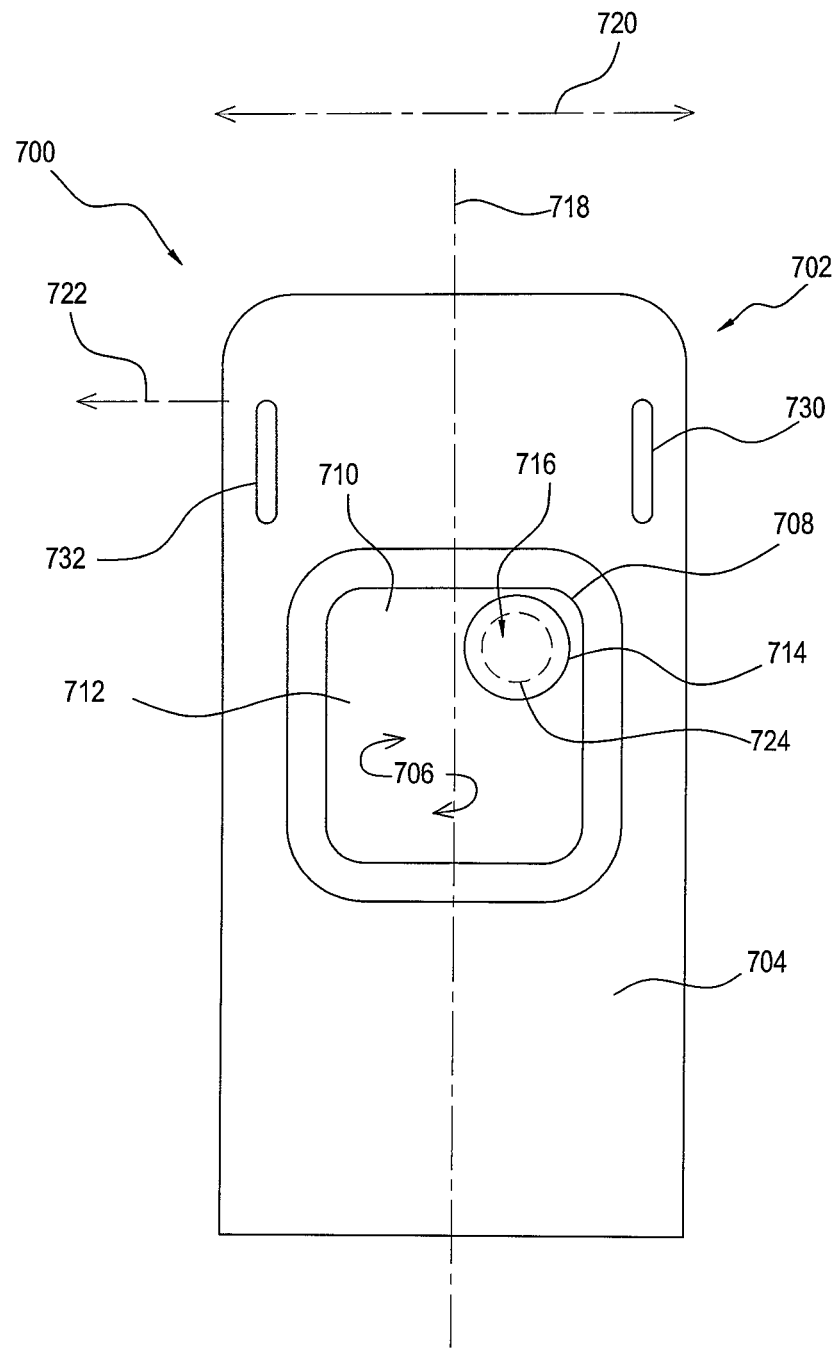
FIG. 7 shows, in schematic proximal elevation, certain features of an exemplary CBBCT imaging system, including a patient interface panel, prepared according to principles of the invention.

FIG. 7 shows, in schematic proximal elevation, certain aspects of an exemplary CBBCT imaging system 700, including a vertical plane gantry subsystem 702, prepared according to principles of the invention. It will be appreciated that vertical plane gantry subsystem 702 is similar in its features to the subsystems discussed above and shows further aspects and details of the same invention, as well as additional inventive features and aspects. Accordingly, vertical plane gantry subsystem 702 includes a patient interface panel 704.

The patient interface panel 704 includes a patient interface surface region 706 adapted to support a patient during scanning. In various embodiments of the invention, the patient interface surface region 706 includes an inner circumferential edge 708 defining an aperture of the patient interface surface region through the patient interface panel. In some embodiments of the invention, the aperture is adapted to receive a breast of the patient disposed therethrough. In other embodiments, including that illustrated in FIG. 7, the aperture is adapted to receive a patient interface subpanel 710 that traverses circumferential edge 708. The patient interface subpanel 710 is coupled to and/or supported by the patient interface panel 704.

In comparing inner circumferential edges, e.g., 244 (FIG. 2) and 708, it will be apparent that the particular shape of the circumferential edge will be selected in a corresponding embodiment so as to optimize considerations such as functionality and ease of manufacture. Accordingly, the geometry shown is merely exemplary of a wide variety of configurations that will be immediately apparent to one of skill in the art in light of the entirety of the present disclosure.

The patient interface subpanel 710 includes a subpanel surface region 712. A further inner circumferential edge 714 defines a subpanel aperture 716 through the subpanel. In the configuration illustrated, the subpanel aperture 716 is disposed to the right of a longitudinal centerline 718 of the patient interface panel 704. Accordingly, in typical operation of the CBBCT imaging system, a right breast of the patient will be disposed through the subpanel aperture 716 during imaging.

With further reference to FIG. 7 and FIG. 3 above, in certain embodiments of the invention, a patient support subsystem 330 will include an exemplary seat apparatus 344. As discussed above, the exemplary seat apparatus 344 is coupled to, and supported by, column member 332. The seat apparatus 344 includes a saddle portion 346 with a structural body member 348 and a saddle upper surface region 350.

As also discussed above, the seat adjustment mechanism permits positional adjustment of the saddle 346 vertically 356 and transverse 358 to a longitudinal axis 360 of the foundation element 336. In certain embodiments, the seat adjustment mechanism also permits pivotal rotations in additional degrees of freedom, i.e. 362 (yaw) of the saddle about a longitudinal axis of the seat column 352 and 363 (pitch) about a transverse axis 358.

Accordingly, the seat adjustment mechanism is adapted to adjust a lateral position of the patient with respect to the patient interface panel 704. Among other degrees of freedom, such a system will permit adjustment of the position of the patient in a dimension 720 transverse to the table centerline 718. This adjustment will, in advantageous application, translate the patient's breast in a direction (i.e., degree of freedom) 722 towards a centerline of the CBBCT imaging system (i.e. towards an axis of rotation, e.g. 306 as described above, of a rotating gantry of the system).

One of skill in the art will appreciate that, in certain embodiments of the invention, a plurality of subpanels will be provided that include apertures of different respective dimensions. For example, a subpanel having an internal circumferential edge 724 defining an aperture with a smaller diameter (as compared with illustrated aperture 716 defined by inner circumferential edge 714) will be available. Accordingly, technical or medical personnel will be able to select and install a subpanel having an aperture appropriate for the size and location of the breast of the particular patient to be imaged.

In other embodiments of the invention, the adjustment of aperture size will be effected by operation of an adjustment mechanism such as an iris leaf diaphragm aperture mechanism (see, e.g., FIGS. 10D-10F below). In certain embodiments the adjustment mechanism will be substantially permanently coupled to the patient interface panel 704 of the vertical plane gantry subsystem 702. In other embodiments of the invention, the adjustment mechanism will be coupled to a subpanel like subpanel 710 described above.

In certain embodiments of the invention, the aperture for receiving the breast to be imaged is disposed generally coincident with the centerline of the patient interface panel.

In such an embodiment, the patient will be positioned to align the breast to be imaged with the centerline of the table. Consequently, no additional transverse mechanism is required to align the breast with the axis of rotation of the gantry. It will be appreciated by one of skill in the art that this alignment of the breast aperture may be effected by providing the aperture directly in the patient interface panel, or, alternately, in a subpanel configured for attachment or coupling to the patient interface panel.

Figure 8:
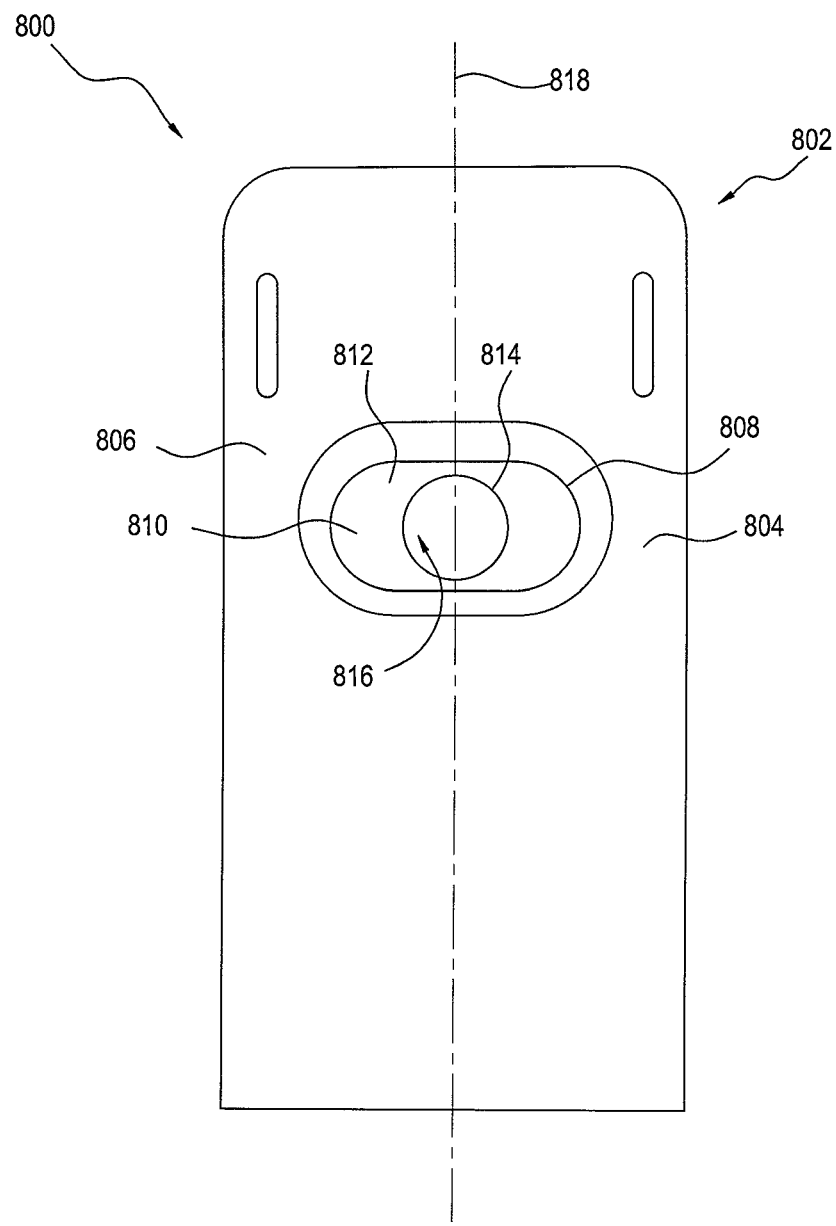
FIG. 8 shows, in schematic proximal elevation, additional features of an exemplary CBBCT imaging system, including a patient interface panel, prepared according to principles of the invention.

Accordingly, FIG. 8 shows, in schematic proximal elevation, certain aspects of an exemplary CBBCT imaging system 800 including, including a vertical plane gantry subsystem 802, generally similar to vertical plane gantry subsystem 702 of FIG. 7. Vertical plane gantry subsystem 802 includes a patient interface panel 804.

The patient interface panel 804 includes a patient interface surface region 806 adapted to support the patient during scanning. In various embodiments of the invention, the patient interface surface region 806 includes an inner circumferential edge 808 defining an aperture of the patient interface surface region through the patient interface panel. Like the exemplary embodiment provided in FIG. 7, the aperture is adapted to receive a subpanel 810 that traverses circumferential edge 808. The subpanel 810 is coupled to and/or supported by the patient interface panel 804.

The subpanel 810 includes a subpanel surface region 812. A further inner circumferential edge 814 defines a subpanel aperture 816 through the subpanel. In the configuration illustrated, the subpanel aperture 816 is disposed coincident with a longitudinal centerline 818 of the patient interface panel 804. Accordingly, in typical operation of the CBBCT imaging system, either breast of the patient may be disposed through the subpanel aperture 816 during imaging, with the seat adjustment mechanism (e.g., that discussed above with respect to FIG. 3) being configured to align the subject breast with the subpanel aperture 816 and the patient being arranged on the upper surface 806 of the patient interface panel 804 accordingly.

Although the inner circumferential edges, e.g., 714, 724, 814 illustrated and discussed above are shown with substantially circular aspects, one of skill in the art will appreciate that the circumferential edge may be of any form considered advantageous according to the requirements of a particular application of the invention. Accordingly, in certain embodiments of the invention, the circumferential edge will be generally elliptical, or may be generally triangular, or of any other regular or irregular polygonal form, or of any arcuate form or any combination of arcuate and linear segments, or any combination of the foregoing, all of which should be deemed to be within the scope of the present disclosure.

Referring again to FIG. 7 the exemplary patient interface panel 704 includes handles 730, 732. The handles 730, 732 are positioned and configured such that a patient is able to grasp the handles during mounting and operation of the CBBCT imaging system 700. This improves the ability of the patient to position the patient's body on the patient interface panel 704, and provides stability to the patient during imaging, resulting in improved data/image quality.

In various embodiments of the invention, handles 730, 732 will be adjustable in one or more of the dimension of centerline 718, in transverse dimension 720, and rotary fashion about a respective vertical axis disposed through the respective handle generally normal to patient interface surface 706 of the patient interface panel 704. The reader will appreciate that the illustrated location and configuration of the exemplary handle presented here is only one of many possible configurations.

Moreover, the location of any handle will, in a corresponding embodiment of the invention, be reconfigurable to be located at any desirable location with respect to the patient interface surface 706 of the patient interface panel 704. Thus, in certain embodiments of the invention, the handle e.g. 730 will be coupled to patient interface surface 706 by a removable magnetic device, by a hook and loop fastener device, by a snap device, by a protrusion and recess device, by an elastic suction cup device, or by any other means or device appropriate to the desired goal of having the handle temporarily but nonetheless effectively fixed in place with respect to patient interface surface 706.

Figure 9A:
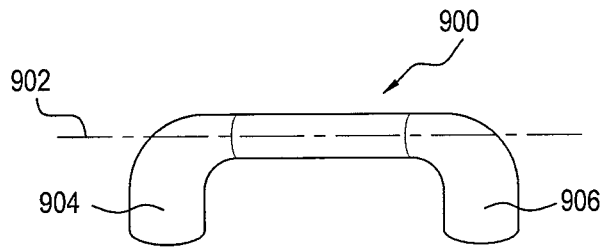
FIG. 9A shows, in schematic perspective view, certain features of a CBBCT imaging system prepared according to principles of the invention, including an exemplary handle.

FIGS. 9A-9E show, in schematic perspective view, exemplary handles that will be employed in respective embodiments of the invention. One of skill in the art will readily appreciate the advantages of the particular handles shown, and of others that are suggested by the present disclosure, and are deemed to be within its scope. For example, FIG. 9A shows a handle 900 adapted to be grasped primarily about a transverse longitudinal axis 902 and to be substantially fixedly coupled to a patient interface panel, directly or through an adjustment apparatus at first 904 and second 906 ends thereof. It will be noted that the handle of FIG. 9A bears some similarity to the handles shown as elements 730, 732 in FIG. 7.

Figure 9B:
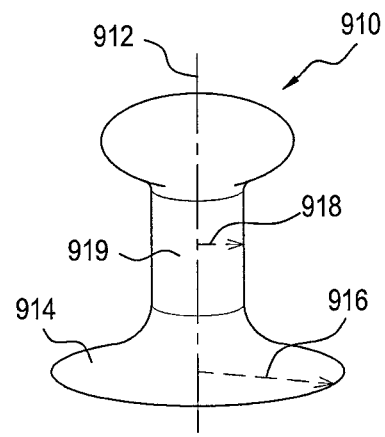
FIG. 9B shows, in schematic perspective view, additional features of a CBBCT imaging system prepared according to principles of the invention, including an exemplary handle.

FIG. 9B shows an alternative handle 910 adapted to be grasped primarily about a longitudinal axis 912 disposed generally normal to a surface of the patient interface panel. A flange portion 914 of the handle 910 has a generally larger radius 916, than a radius 918 of a grip portion 919. This extended flange provides for effective coupling to the patient interface panel, as well as improved stability and rigidity of the handle 910.

Figure 9C:
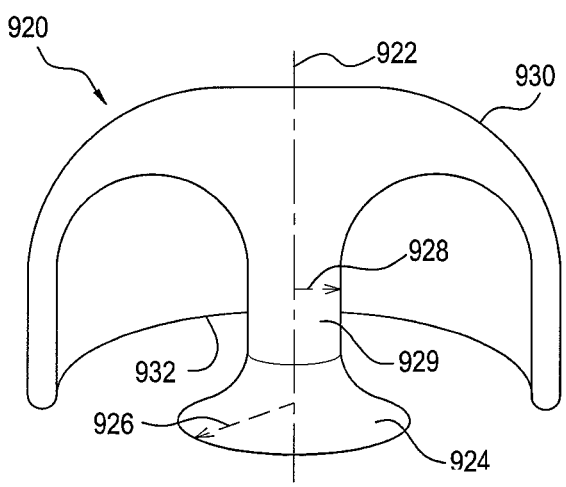
FIG. 9C shows, in schematic perspective view, still further features of a CBBCT imaging system prepared according to principles of the invention, including an exemplary handle.

FIG. 9C shows a further alternative handle 920 adapted to be grasped primarily about a longitudinal axis 922 disposed generally normal to a surface of the patient interface panel. A lower flange portion 924 of the handle 920 has a generally larger radius 926, than a radius 928 of a grip portion 929. An upper flange portion 930 is disposed in arcuate fashion away from the longitudinal axis 922, and downward towards the patient interface panel to which it couples at a lower edge 932 thereof. The extended lower and upper flanges provide for effective coupling of the handle 920 to the patient interface panel, as well as improved stability and rigidity of the handle.

Figure 9D:
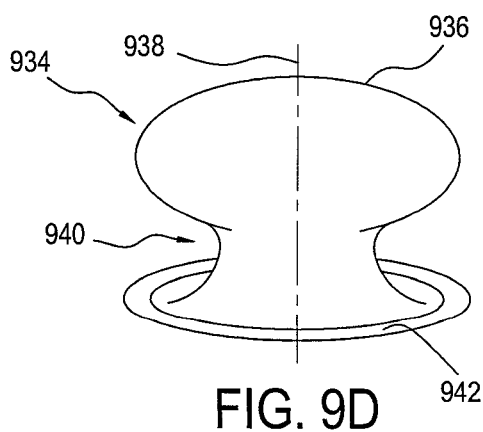
FIG. 9D shows, in schematic perspective view, yet other features of a CBBCT imaging system prepared according to principles of the invention, including an exemplary handle.

FIG. 9D shows a further alternative handle 934 adapted to be grasped primarily about a bulbous upper surface 936 disposed generally parallel to a surface of the patient interface panel and transverse to a longitudinal axis 938 of the handle 934. The longitudinal axis 938 is disposed generally normal to the surface of the patient interface panel and, when in use, passes generally through the palm and/or joints of the patient's hand. A circumferential recess 940 disposed below the bulbous upper surface 936 and generally transverse to longitudinal axis 938 is adapted to receive the tips of the patient's fingers therewithin, enhancing patient grip. A lower flange portion 942 of the handle 934 provides for effective coupling of the handle 934 to the patient interface panel, as well as improved stability and rigidity of the handle.

Figure 9E:
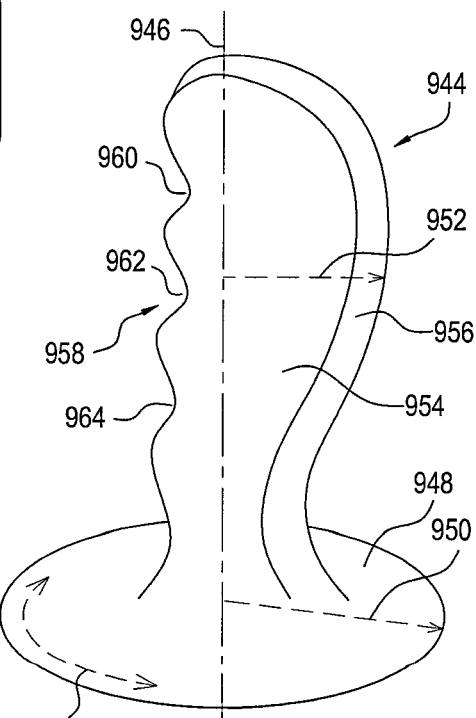
FIG. 9E shows, in schematic perspective view, still more aspects and features of a CBBCT imaging system prepared according to principles of the invention, including an exemplary handle.

FIG. 9E shows a further alternative handle 944 adapted to be grasped primarily about a longitudinal axis 946 disposed generally normal to a surface of the patient interface panel. A lower flange portion 948 of the handle 944 has a generally larger radius 950, than a lateral dimension 952 of a grip portion 954. One vertical surface region 956 of the handle 944 is generally convex and adapted to be placed in contact with a palm of a patient.

The opposing vertical surface region 958 includes a plurality of concave recesses, e.g., 960, 962, 964, each adapted to receive a respective finger of the patient disposed therewithin. In certain embodiments, the handle 944 is substantially fixedly coupled to a patient interface panel of the patient support panel. In other embodiments, the handle is coupled to the patient interface panel through a rotary bearing and adapted to pivot circumferentially 966 substantially freely, or to be adjusted by pivoting circumferentially 966 and then releasably fixed in place, according to the requirements of a particular application of the invention. This pivotal motion allows adjustment of the position of surfaces 956 and 958 for optimum comfort of a patient grasping the handle.

In the context of the foregoing discussions, FIGS. 10A-10F show, in schematic fashion, a variety of exemplary subpanel configurations that fall within the scope of the present invention and are similar to subpanels 710 and 810 described above in relation to FIGS. 7 and 8.

Figure 10A:
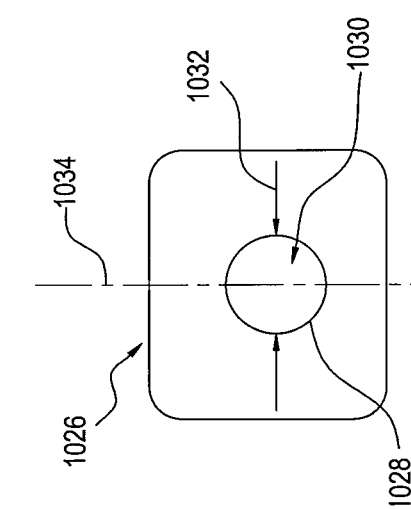
FIG. 10A shows, in schematic proximal elevation, certain features of a CBBCT imaging system prepared according to principles of the invention, including exemplary subpanel elements.
Figure 10B:
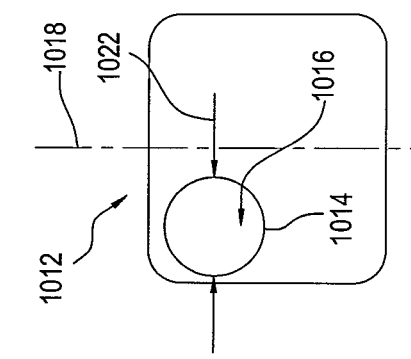
FIG. 10B shows, in schematic proximal elevation, additional aspects of a CBBCT imaging system prepared according to principles of the invention, including exemplary subpanel elements.
Figure 10C:
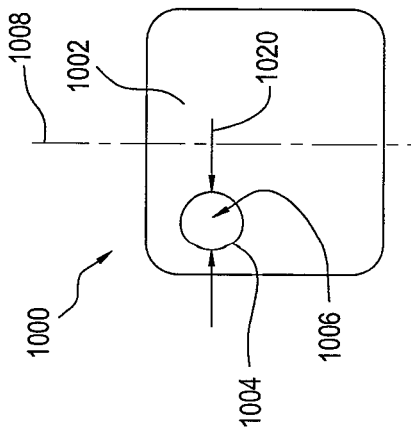
FIG. 10C shows, in schematic proximal elevation, further exemplary aspects of a CBBCT imaging system prepared according to principles of the invention, including exemplary subpanel elements.

FIGS. 10A-10C show respectively, in schematic elevation, exemplary subpanels having a variety of aperture locations and sizes.

Referring first to FIG. 10A, subpanel 1000 includes a subpanel surface region 1002. An inner circumferential edge 1004 defines a subpanel aperture 1006 through the subpanel. Consistent with the discussion above, the aperture 1006 is adapted to receive a patient breast to be imaged therethrough. In the configuration illustrated, the subpanel aperture 1006 is disposed to the left of a longitudinal centerline 1008 of the subpanel 1000. Accordingly, in typical operation of the CBBCT imaging system, a left breast of the patient will be disposed through the subpanel aperture 1006 during imaging.

FIG. 10B shows a subpanel 1012 similar to subpanel 1000. As with subpanel 1000, subpanel 1012 has an inner circumferential edge 1014 that defines a subpanel aperture 1016 through the subpanel 1012. Like aperture 1006, aperture 1016 is disposed to the left of a longitudinal centerline 1018 of the subpanel 1012. However, aperture 1006 has a diameter 1020 that is relatively smaller than the corresponding diameter 1022 of aperture 1016.

FIG. 10C shows a subpanel 1026 similar to subpanels 1000 and 1012. As with subpanel 1000, subpanel 1026 has an inner circumferential edge 1028 that defines a subpanel aperture 1030 through the subpanel 1026. Aperture 1030 has a diameter 1032 that is substantially equal to corresponding diameter 1022 of aperture 1016. However, a centroid of aperture 1030 is disposed substantially coincident with centerline 1034 of the subpanel 1026. Accordingly, whereas apertures 1006 and 1016 are primarily configured for receiving a left breast of the patient for imaging, aperture 1030 is well adapted to receiving either a left breast or a right breast.

It will also be appreciated by one of skill in the art that, where appropriate perimeter configurations and coupling features are provided, symmetries of the illustrated panels will be used in respective embodiments of the invention to image, for example, either a left breast or a right breast by symmetric rotation of subpanel 1000 or 1012 about centerlines 1008 and 1018 respectively.

Likewise, rotation of the panels about an axis transverse to the centerlines can be used to locate the illustrated apertures relatively higher or lower respectively, according to the needs of a taller or shorter patient.

In light of the foregoing discussion, it will be appreciated by the reader that, in certain embodiments of the invention, a plurality of subpanels will be provided along with an imaging system, such that the subpanel with the appropriate aperture will be selected according to the height, weight, breast size and other parameters of the patient.

In another embodiment of the invention, individual reusable subpanels will be purchased so as to be available where required. In still other embodiments of the invention, disposable subpanels will be employed for single use with a respective patient, and thereafter discarded.

Figure 10D:
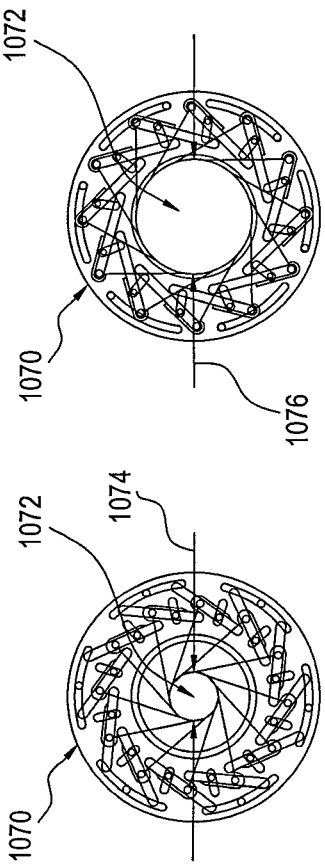
FIG. 10D shows, in schematic proximal elevation, certain features of a CBBCT imaging system prepared according to principles of the invention, including exemplary adjustable subpanel elements.
Figure 10E:
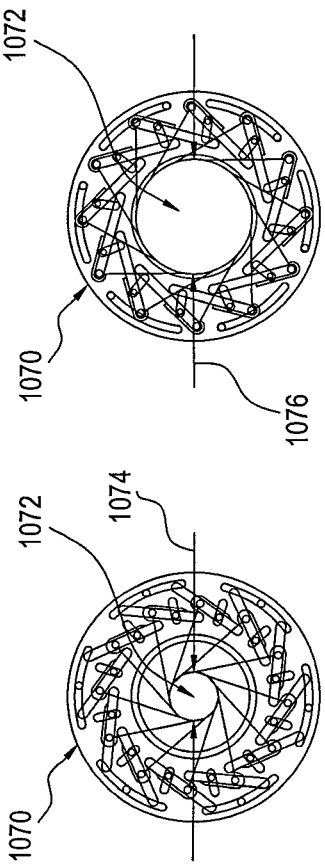
FIG. 10E shows, in schematic proximal elevation, further details of a CBBCT imaging system prepared according to principles of the invention, including exemplary adjustable subpanel elements.
Figure 10F:
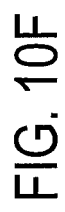
FIG. 10F shows, in schematic proximal elevation, additional configurations of a CBBCT imaging system prepared according to principles of the invention, including exemplary adjustable subpanel elements.

FIGS. 10D-10F show schematic representations of a further subpanel 1050 prepared according to principles of the invention. Subpanel 1050 is shown in cutaway view, and illustrates an adjustment mechanism 1052 included in subpanel 1050.

In the exemplary embodiment illustrated, adjustment mechanism 1052 includes a mechanical iris mechanism 1054. The adjustable iris mechanism 1054 includes a plurality of leaf elements, e.g., 1056, 1058 respectively coupled to corresponding operative links 1060, 1062. One of skill in the art will recognize the adjustable iris mechanism 1054 as similar in form and function to iris mechanisms employed in photographic cameras. Accordingly, by operation of the operative links 1060, 1062, the leaf elements 1056, 1058 will be urged to pivot so as to adjust a diameter of an aperture 1064 to a preferred value according to the requirements for imaging a particular patient breast.

By way of further illustration, in FIG. 10E exemplary iris mechanism 1070 is adjusted and configured to present an aperture 1072 having a relatively small diameter 1074. In FIG. 10F, exemplary iris mechanism 1070 is adjusted and configured to present the same aperture 1072 with a relatively large diameter 1076.

Figure 11:
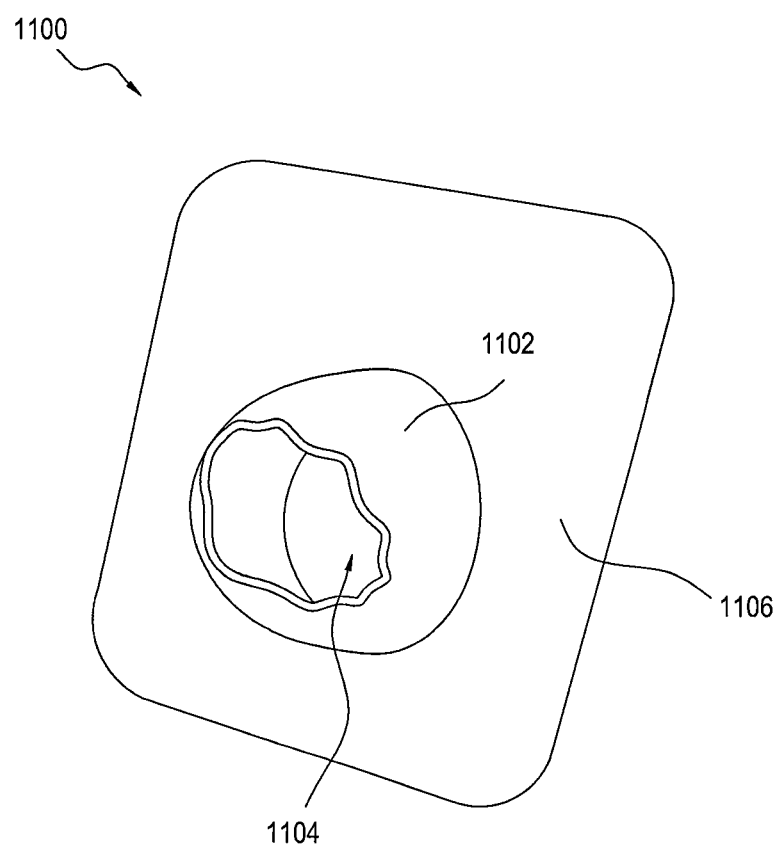
FIG. 11 shows, in schematic perspective view, certain further features of a CBBCT imaging system prepared according to principles of the invention, including exemplary breast stabilization features.

In a still further aspect of the invention FIG. 11 shows, in schematic distal cutaway perspective view, a subpanel 1100 including a breast stabilizer unit 1102 adapted and configured to support and stabilize a patient breast during imaging. As illustrated, the breast stabilizer unit 1102 is coupled to the subpanel 1100 at aperture 1104 of distal surface 1106.

One of skill in the art will readily appreciate the various benefits and modalities for employing a breast stabilizer unit like the exemplary stabilizer unit presented herewith upon review of the related applications listed above.

Figure 12:
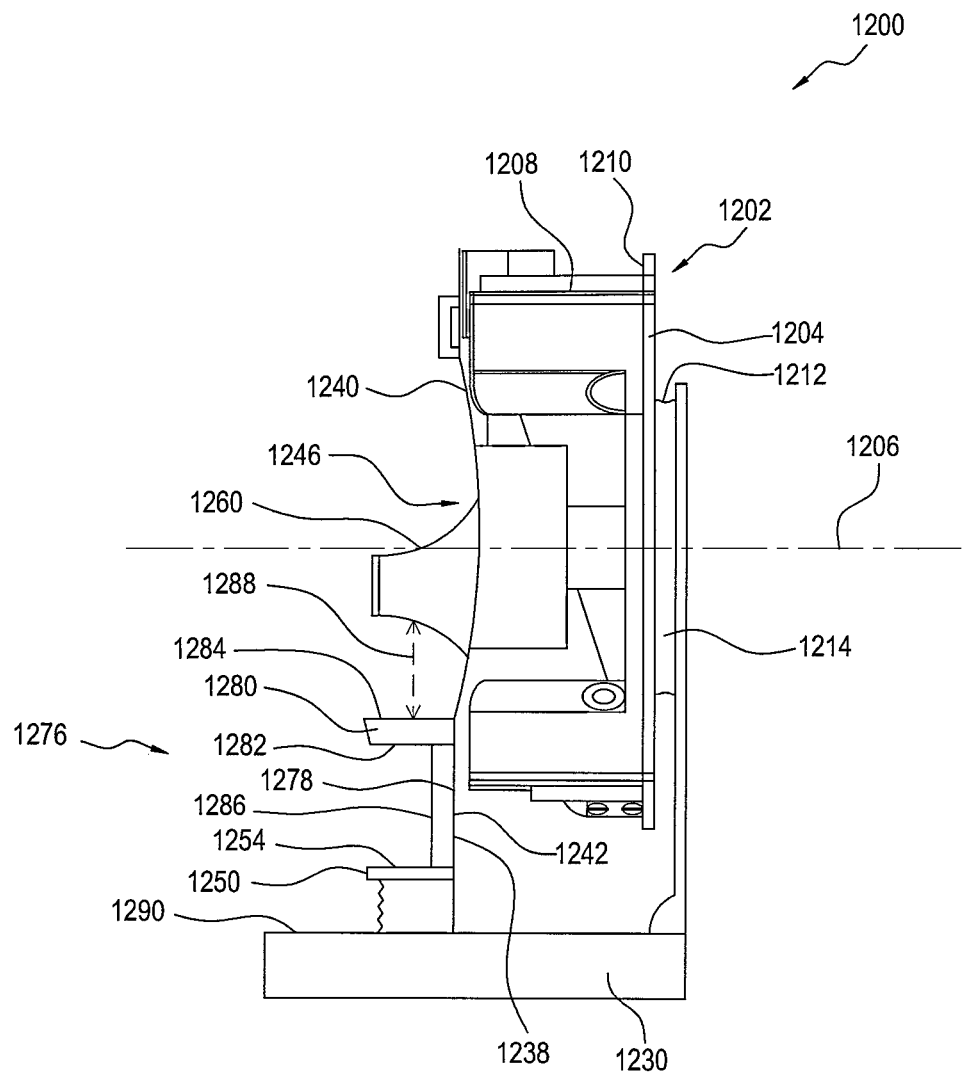
FIG. 12 shows, in schematic side elevation, additional aspects and configurations of an exemplary CBBCT imaging system, including a patient support saddle feature prepared according to principles of the invention.

FIG. 12 shows, in schematic side elevation, a portion of an exemplary CBBCT imaging system 1200, similar to system 200, including a vertical plane gantry subsystem 1202. The vertical plane gantry subsystem 1202 includes a vertical plane gantry 1204 configured to rotate about a generally horizontal axis of rotation 1206.

Like systems 100 and 200 described above, system 1200 includes an x-ray source 1208. The exemplary x-ray source 1208 is mounted on, and supported by, a mounting surface 1210 of the vertical plane gantry 1204. The vertical plane gantry 1204 is supported by a bearing 1212, and arranged for rotation about the axis of rotation 1206. The bearing 1212 is, in turn, coupled to and supported by a structural member 1214.

A base member 1230 is coupled to the structural member 1214. A patient interface panel 1238 is coupled through the base member 1230 to the structural member 1214 so that the structural member 1214 and the base member 1230 serve to support the patient interface panel 1238.

The patient interface panel 1238 has a first patient interface surface region 1240 and a second distal surface region 1242, where the distal surface region 1242 is disposed in spaced relation to the patient interface surface region 1240.

The exemplary patient interface panel 1238 is similar in form and function to the patient interface panel 238 of FIG. 2.

Accordingly, referring to FIGS. 2 and 12 the patient interface panel includes an internal circumferential edge of the patient interface surface region. The internal circumferential edge circumscribes an aperture 1246 through the patient interface panel 1238 between patient interface surface region 1240 and distal surface region 1242.

In a manner similar to that described above, the patient interface surface region 1240 is arranged to segregate the patient from the balance of the vertical gantry subsystem 1202 with a breast of the patient disposed through the aperture 1246. In various embodiments and aspects of the invention, a patient interface subsystem, as exemplified above, is disposed at the aperture 1246. In various aspects, the patient interface subsystem will provide one or more of an aperture sized and located according to the particular patient and breast being imaged, shielding for regions of the patient that might otherwise be exposed to scattered x-ray photons, and support and stabilization of the breast being imaged, among other features.

The CBBCT imaging system 1200 also includes an exemplary seat apparatus 1276. In the illustrated embodiment, exemplary seat apparatus 1276 is coupled to, and supported by, a corresponding portion 1278 of the patient interface surface region 1240. In other embodiments of the invention, the exemplary seat apparatus 1276 is coupled to and supported by base portion 1230, and/or patient step 1250, or to any other location, feature or aspect of the CBBCT imaging system, or combination of the same, appropriate to the requirements of a particular application and embodiment of the invention.

The seat apparatus 1276 includes a saddle portion 1280 with a structural body member 1282 a saddle upper surface region 1284. Saddle upper surface region 1284 is adapted to position and support a patient sitting astride the saddle portion 1280 during imaging as well as during optional supplemental procedures.

In the illustrated embodiment, structural body member 1282 is substantially fixedly coupled to an upper end of an exemplary seat column 1286 which is coupled to the CBBCT imaging system 1200 as described above, directly or through an appropriate positional adjustment apparatus. The seat column is optional, and in certain embodiments of the invention, the saddle structural body member is coupled directly to the CBBC to imaging system 1200.

Accordingly, in certain embodiments of the invention, a lower end of the exemplary seat column 1286 is operatively coupled to a seat adjustment mechanism. The seat adjustment a mechanism is coupled, directly or indirectly, to the base member 1230 for support. Consequently, the weight of a patient seated on the saddle upper surface region 1284 is transferred through the structural body member 1282 of the saddle to the seat column 1286, and from there through the seat adjustment mechanism to the base member 1230.

In a desirable aspect of certain embodiments of the invention, the seat adjustment mechanism permits positional adjustment of the saddle portion 1280 vertically 1288 i.e., transverse to an upper surface 1290 of the base member 1230. In certain embodiments, the seat adjustment mechanism also permits pivotal rotations in additional degrees of freedom i.e., yaw of the saddle about a longitudinal axis of the seat column 1286 as well as pitch and roll about respective axes.

Beyond this, in certain embodiments of the invention, roll of the saddle portion 1280 will also be adjustable to ensure comfort and optimal positioning of the patient with respect to the vertical plane gantry subsystem 1202.

In a still further aspect of the invention, in certain embodiments the saddle will be removable or foldable, or otherwise displaceable so that a patient being imaged will not sit on the saddle, but will stand on an upper surface 1254 of the step portion 1250, for example. Accordingly, seating on the saddle will be available where desirable, but the saddle need not be employed where a standing mode of patient support is preferable.

As will be appreciated by one of skill in the art, the saddle portion 1276 will be shaped and configured to promote optimal comfort and positioning of the patient with respect to the vertical plane gantry subsystem 1202. In certain embodiments, the saddle portion 1276 will include materials that advantageously are biocompatible and exhibit desirable characteristics of rheology and elastic durometer.

Accordingly, in respective embodiments of the invention, the saddle portion 1276 will include materials appropriate to achieve these ends. A variety of exemplary materials corresponding to respective embodiments of the invention are provided above in relation to the description accompanying FIG. 3.

In the illustrated embodiment, the patient interface panel 1238 is coupled to, and supported by, the base member 1230 of the vertical plane gantry subsystem 1202. In other embodiments of the invention, as further described herewith, alternative features of the imaging system will support the patient interface panel.

Figure 13A:
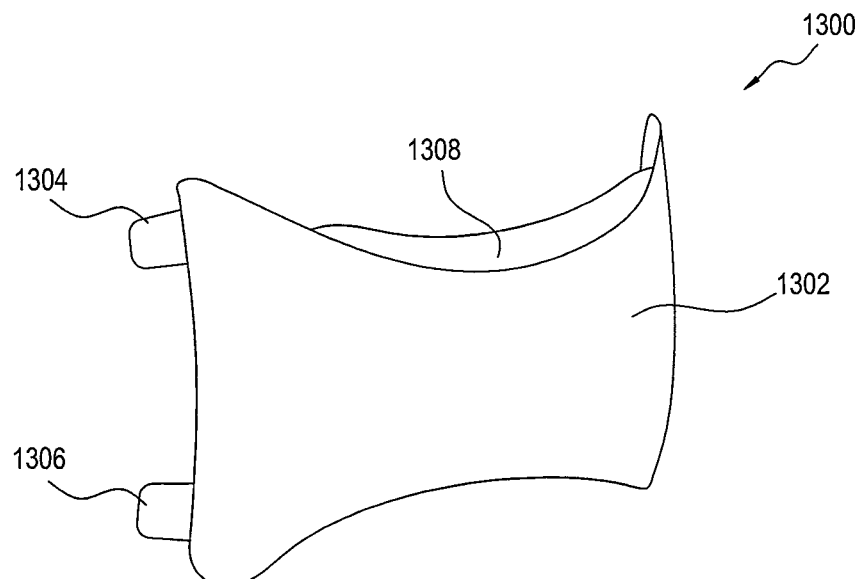
FIG. 13A shows, in elevated schematic perspective view, certain aspects of an exemplary CBBCT imaging system, including certain safety features thereof prepared according to principles of the invention.
Figure 13B:
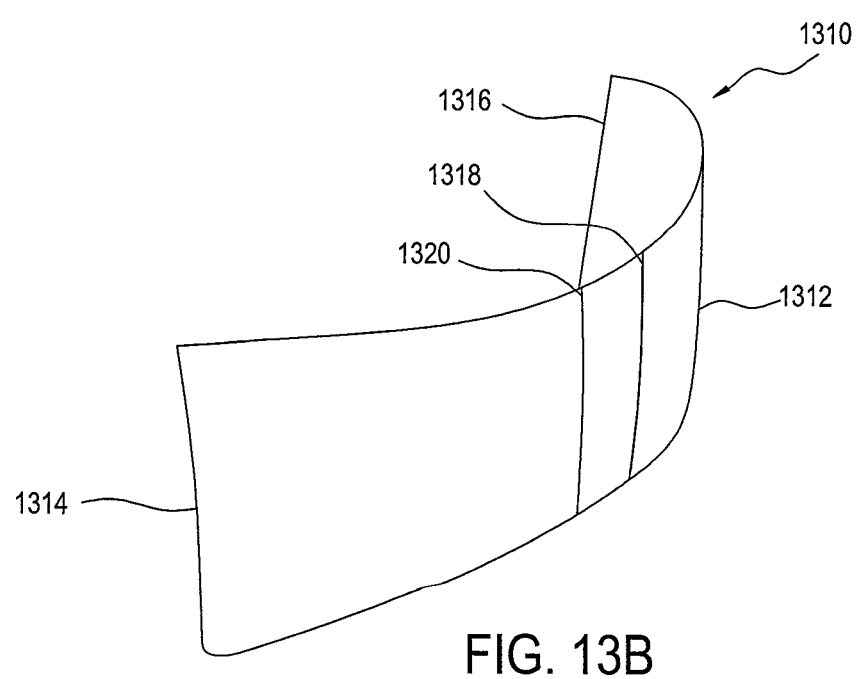
FIG. 13B shows, in elevated schematic perspective view, certain aspects of an exemplary CBBCT imaging system, including additional safety features thereof prepared according to principles of the invention.

FIGS. 13A and 13B show, in schematic perspective view, safety elements exemplary of safety feature 1260 of CBBCT imaging system 1200.

FIG. 13A shows a safety belt 1300 for a CBBCT imaging system. Safety belt 1300 includes a generally flexible member 1302. In the illustrated embodiment, flexible member 1302 includes, for example, a textile material such as, for example, a woven textile material, a knitted textile material, a felted textile material, or a chain-linked textile material. In other embodiments of the invention, the flexible member 1302 includes one or more of a molded elastomeric polymer, a spray-formed elastomeric polymer a rope or cable, a natural material such as a natural polymer, a leather, a vegetable material, or other material or combination of materials appropriate to the objectives and functions described herewith.

The illustrated safety belt 1300 includes a coupling mechanism e.g., 1304, 1306 adapted for detachably coupling the safety belt 1300 to the patient interface panel 1238. In various embodiments of the invention, the coupling mechanism 1304, 1306 will include one or more of a buckle, a button, a hook and loop fastener, a mechanical snap fastener, a magnet fastener, an adhesive fastener, or any other fastener appropriate to the purposes in light of the present disclosure that is known or becomes known in the art, as well as combinations of the same.

In certain embodiments of the invention, the safety belt 1300 will include a cushion element 1308. In certain embodiments, the cushion element will include a generally elastic element that serves to distribute forces across an inner surface of the flexible element 1302, operative to avoid excessive pressure at points of contact with the patient's back.

In certain embodiments of the invention, the cushion element 1308 will include an expanding element such as for example, an air bladder, a liquid bladder, or a mechanical actuator. In certain embodiments of the invention, the expanding element is adapted to expand in a controlled fashion once the safety belt is coupled to the patient interface panel 1238, thereby urging the patient against the patient interface surface 1240.

FIG. 13B shows an alternative safety belt 1310 for a CBBCT imaging system. Like safety belt 1300, safety belt 1310 includes a generally flexible member 1312. In the illustrated embodiment, flexible member 1312 includes, for example, a textile material and/or any of the materials provided as examples above.

The flexible member 1312 has a first end 1314 and a second end 1316 that are adapted to be coupled to respective regions of patient interface panel 1238. In certain embodiments of the invention, the respective ends 1314 and 1316 are substantially permanently coupled to the patient interface panel 1238. In other embodiments of the invention, ends 1314 and 1316 are removably and/or adjustably coupled to the patient interface panel 1238.

In the illustrated embodiment, the flexible member 1312 has third 1318 and fourth 1320 internal ends that are adapted to be releasably coupled to each other. Accordingly, internal ends 1318, 1320 will include respective complementary coupling features. Thus, for example, internal ends 1318, 1320 will include respective complementary portions of a buckle, a button, a hook and loop fastener, a mechanical snap fastener, a magnet fastener, or any other fastener appropriate to the purposes in light of the present disclosure that is known or becomes known in the art, as well as combinations of the same.

In certain embodiments of the invention, the safety belts 1300, 1310 will include, for example, a polymer material such as, for example, polyamide, or polyaramid.

In other embodiment of the invention, the safety belt 1300, 1310, including elements of its assembly, will include one or more of polyethylene, polypropylene, polybutylene, polystyrene, polyester, acrylic polymers, polyvinylchloride, polyamide, or polyetherimide like ULTEM.RTM.; a polymeric alloy such as Xenoy.RTM. resin, which is a composite of polycarbonate and polybutyleneterephthalate or Lexan.RTM. plastic, which is a copolymer of polycarbonate and isophthalate terephthalate resorcinol resin (all available from GE Plastics), liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, polyesterimide anhydrides with terminal anhydride group or lateral anhydrides.

In addition, any polymeric composite such as engineering prepregs or composites, which are polymers filled with pigments, carbon particles, silica, glass fibers, conductive particles such as metal particles or conductive polymers, or mixtures thereof may also be used. For example, a blend of polycarbonate and ABS (Acrylonitrile Butadiene Styrene) may be used.

The apparatus of the cone beam breast CT acquires two-dimensional projection data. Acquisition geometries can be a single circle geometry, double circle geometry (for a large size of breast), a circle-plus-line geometry, half-circle-plus cone angle geometry, spiral cone beam geometry. One or more of these geometries are then employed to construct CBBCT 3D images from the 2D projection data. The reconstruction methods can be filtered backprojection, iterative algorithms, and/or AI deep learning algorithms. The specialized imaging processors can be used to perform the fast reconstruction and imaging processing.

In certain embodiments the CBBCT scanning system comprises a foundation element, including a vertical plane gantry subsystem coupled to and supported by the foundation element. The vertical plane gantry subsystem includes a CBBCT gantry, the CBBCT gantry being adapted and configured to rotate about a generally horizontal axis of rotation, the vertical plane gantry subsystem includes a patient interface panel, the patient interface panel having a patient interface surface region with an aperture therethrough, the vertical plane gantry subsystem includes a patient support subpanel disposed within the aperture of the patient interface panel, and a patient support subsystem coupled to and supported by the foundation element. The patient support system includes a saddle portion and a back portion, the saddle portion has a saddle upper surface region, the saddle upper surface region being adapted and configured to support a patient seated thereon in proximity to the patient interface surface region. The back portion includes an active back support mechanism, the active back support mechanism being adapted, when activated, to urge the patient towards the patient interface surface region and adapted to position and stabilize the breast of the patient during CBBCT imaging of the breast of the patient.

In certain embodiments the active back support mechanism of the CBBCT scanning system comprises a pneumatic bladder, in some embodiments the active back support mechanism comprises a hydraulic bladder, while in certain embodiments the active back support mechanism comprises a patient-controlled release mechanism.

In some embodiments the saddle portion of the CBBCT scanning system is coupled to a seat adjustment mechanism.

In certain embodiments the seat adjustment mechanism of the CBBCT scanning system is adapted to adjust the saddle upper surface region of the saddle portion in a vertical degree of freedom while in certain embodiments the seat adjustment mechanism is adapted to adjust the saddle upper surface region of the saddle portion in a horizontal degree of freedom.

In certain embodiments the seat adjustment mechanism of the CBBCT scanning system is adapted to adjust the saddle upper surface region of the saddle portion in a pitch degree of freedom while in certain embodiments the seat adjustment mechanism is adapted to adjust the saddle upper surface region of the saddle portion in a roll degree of freedom and in still further embodiments the seat adjustment mechanism is adapted to adjust the saddle upper surface region of the saddle portion in a yaw degree of freedom.

In certain embodiments of the invention a method of conducting a CBBCT scan comprises providing an imaging system including a foundation element, providing a vertical plane gantry subsystem coupled to the foundation element, providing a patient support subsystem coupled to the foundation element, disposing the imaging system in a first distal configuration with respect to a distance between the patient support subsystem and the vertical plane gantry subsystem, adjusting a patient support subsystem parameter for patient positioning, seating a patient on a saddle of the patient support subsystem, disposing the imaging system in a second proximal configuration with respect to the distance between the patient support subsystem and the vertical plane gantry subsystem, positioning a patient breast within the vertical plane gantry subsystem, engaging a back support mechanism of the patient support subsystem, urging the patient towards the vertical plane gantry subsystem, CBBCT scanning the patient breast with the vertical plane gantry subsystem, releasing the back support mechanism of the patient support subsystem, returning the imaging system to the first distal configuration, and dismounting the patient from the saddle of the patient support subsystem.

In certain embodiments of the invention a method of conducting a CBBCT scan further comprises providing a patient interface panel, the patient interface panel has a subpanel aperture therethrough, installing a patient support subpanel at the subpanel aperture and disposing a patient breast through a breast aperture of the patient support subpanel.

In certain embodiments of the invention a method of conducting a CBBCT scan further comprises receiving a patient parameter value and selecting the patient support subpanel according to the patient parameter value.

In some embodiments of the invention selecting the patient support subpanel according to the patient parameter value comprises selecting the patient support subpanel to have a breast aperture diameter corresponding to a breast diameter value of the patient breast.

In still further embodiments of the invention selecting the patient support subpanel according to the patient parameter value comprises selecting the patient support subpanel to have a breast aperture beneficially disposed to one side of a centerline of the patient interface panel.

In certain embodiments of the invention a method of conducting a CBBCT scan includes receiving a patient parameter value, and selecting the patient support subpanel to install according to the patient parameter value.

In some embodiments of the invention a method of conducting a CBBCT includes adjusting a diameter of the breast aperture of the patient support subpanel.

In certain embodiments of the invention disposing the patient breast through the breast aperture of the patient support subpanel includes positioning the patient breast within a breast stabilization unit of the patient support subpanel.

In some embodiments of the invention engaging the back support mechanism of the patient support subsystem involves inflating a pneumatic bladder element of the back support mechanism.

In certain embodiments of the invention engaging the back support mechanism of the patient support subsystem includes energizing an electric motor within the back support mechanism and operating an electric motor to extend a scissors linkage mechanism within the patient support subsystem.

In some embodiments of the invention adjusting the patient support subsystem parameter for patient positioning includes adjusting a height of the saddle with respect to an upper surface of the foundation element, while in some embodiments of the invention include adjusting a pitch of the saddle with respect to an upper surface of the foundation element.

Some embodiments of the invention include seating a patient on the saddle of the patient support subsystem and engaging a safety feature of the patient support subsystem.

In some embodiments of the invention engaging the safety feature includes fastening a safety belt of the patient support subsystem.

Certain embodiments of the invention include manually advancing the vertical plane gantry subsystem from the distal configuration to the proximal configuration while certain embodiments automatically advance the vertical plane gantry subsystem from a distal configuration to a proximal configuration.

Some embodiments of the invention include operating a stationary scan subsystem of the vertical plane gantry subsystem to capture a stationary scan of a patient breast.

Some embodiments of the invention include operating a biopsy guidance subsystem of the vertical plane gantry subsystem to guide a manual biopsy procedure of a patient breast.

In certain embodiments of the invention a CBBCT scanning system comprises a foundation element, a vertical plane gantry subsystem coupled to and supported by the foundation element, the vertical plane gantry subsystem includes a patient interface panel, the patient interface panel has a patient interface surface region with an aperture therethrough and a patient support subsystem coupled to and supported by the foundation element, the patient support subsystem includes a saddle, the saddle being adapted and configured to support a patient seated thereon in proximity to the patient interface surface region during a CBBCT scan of a breast of the patient wherein the foundation element is adapted to support the vertical plane gantry subsystem and the patient support subsystem in horizontal motion with respect to one another.

While the exemplary embodiments described above have been chosen primarily from the field of apparatus, and corresponding systems and methods in the operation of a CBBCT imaging system, including ergonomically improved systems and methods thereof, one of skill in the art will appreciate that the principles of the invention are equally well applied, and that the benefits of the present invention are equally well realized in a wide variety of other imaging technologies, for example, imaging of other body parts and imaging of other subjects such as industrial and technological products. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. A CBBCT scanning system comprising:
a foundation element;
a vertical plane gantry subsystem coupled to and supported by said foundation element, said vertical plane gantry subsystem including a CBBCT gantry, said CBBCT gantry being adapted and configured to rotate about a generally horizontal axis of rotation, said vertical plane gantry subsystem including a patient interface panel, said patient interface panel having a patient interface surface region with an aperture therethrough, said vertical plane gantry subsystem including a patient support subpanel disposed within said aperture of said patient interface panel; and
a patient support subsystem coupled to and supported by said foundation element, said patient support system including a saddle portion and a back portion, said saddle portion having a saddle upper surface region, said saddle upper surface region being adapted and configured to support a patient seated thereon in proximity to said patient interface surface region, said back portion including an active back support mechanism, said active back support mechanism being adapted, when activated, to urge said patient towards said patient interface surface region and adapted to position and stabilize said breast of said patient during CBBCT imaging of said breast of said patient.

2. A CBBCT scanning system as defined in claim 1 wherein said active back support mechanism comprises a pneumatic bladder.

3. A CBBCT scanning system as defined in claim 1 wherein said active back support mechanism comprises a hydraulic bladder.

4. A CBBCT scanning system as defined in claim 1 wherein said active back support mechanism comprises a patient-controlled release mechanism.

5. A CBBCT scanning system as defined in claim 1 wherein said saddle portion is coupled to a seat adjustment mechanism.

6. A CBBCT scanning system as defined in claim 5 wherein said seat adjustment mechanism is adapted to adjust said saddle upper surface region of said saddle portion in a vertical degree of freedom.

7. A CBBCT scanning system as defined in claim 5 wherein said seat adjustment mechanism is adapted to adjust said saddle upper surface region of said saddle portion in a horizontal degree of freedom.

8. A CBBCT scanning system as defined in claim 5 wherein said seat adjustment mechanism is adapted to adjust said saddle upper surface region of said saddle portion in a pitch degree of freedom.

9. A CBBCT scanning system as defined in claim 5 wherein said seat adjustment mechanism is adapted to adjust said saddle upper surface region of said saddle portion in a roll degree of freedom.

10. A CBBCT scanning system as defined in claim 5 wherein said seat adjustment mechanism is adapted to adjust said saddle upper surface region of said saddle portion in a yaw degree of freedom.

11. A method of conducting a CBBCT scan comprising:
providing an imaging system including a foundation element;
providing a vertical plane gantry subsystem coupled to said foundation element;
providing a patient support subsystem coupled to said foundation element;
disposing said imaging system in a first distal configuration with respect to a distance between said patient support subsystem and said vertical plane gantry subsystem;
adjusting a patient support subsystem parameter for patient positioning;
seating a patient on a saddle of said patient support subsystem;
disposing said imaging system in a second proximal configuration with respect to said distance between said patient support subsystem and said vertical plane gantry subsystem;
positioning a patient breast within said vertical plane gantry subsystem;
engaging a back support mechanism of said patient support subsystem;
urging said patient towards said vertical plane gantry subsystem;
CBBCT scanning said patient breast with said vertical plane gantry subsystem;
releasing said back support mechanism of said patient support subsystem;
returning said imaging system to said first distal configuration; and
dismounting said patient from said saddle of said patient support subsystem.

12. A method of conducting a CBBCT scan as defined in claim 11 further comprising:

providing a patient interface panel, said patient interface panel having a subpanel aperture therethrough;

installing a patient support subpanel at said subpanel aperture; and disposing said patient breast through a breast aperture of said patient support subpanel.

13. A method of conducting a CBBCT scan as defined in claim 12 further comprising:

receiving a patient parameter value; and selecting said patient support subpanel according to said patient parameter value.

14. A method of conducting a CBBCT scan as defined in claim 13 wherein said selecting said patient support subpanel according to said patient parameter value comprises:

selecting said patient support subpanel to have a breast aperture diameter corresponding to a breast diameter value of said patient breast.

15. A method of conducting a CBBCT scan as defined in claim 13 wherein said selecting said patient support subpanel according to said patient parameter value comprises:

selecting said patient support subpanel to have a breast aperture beneficially disposed to one side of a centerline of said patient interface panel.

16. A method of conducting a CBBCT scan as defined in claim 12 further comprising:

receiving a patient parameter value; and wherein said installing said patient support subpanel further comprises:

selecting said patient support subpanel according to said patient parameter value.

17. A method of conducting a CBBCT scan as defined in claim 12 further comprising:

adjusting a diameter of said breast aperture of said patient support subpanel.

18. A method of conducting a CBBCT scan as defined in claim 12 wherein said disposing said patient breast through said breast aperture of said patient support subpanel comprises:

positioning said patient breast within a breast stabilization unit of said patient support subpanel.

19. A method of conducting a CBBCT scan as defined in claim 11 wherein said engaging said back support mechanism of said patient support subsystem further comprises:

inflating a pneumatic bladder element of said back support mechanism.

20. A method of conducting a CBBCT scan as defined in claim 11 wherein said engaging said back support mechanism of said patient support subsystem further comprises:

energizing an electric motor within said back support mechanism; and operating said electric motor to extend a scissors linkage mechanism within said patient support subsystem.

* * * * *